(12) United States Patent
Fukuchi

(10) Patent No.: US 11,143,766 B2
(45) Date of Patent: Oct. 12, 2021

(54) PET SYSTEM WITH A POSITRON LIFETIME MEASUREMENT FUNCTION AND POSITRON LIFETIME MEASUREMENT METHOD IN A PET SYSTEM

(71) Applicant: RIKEN, Saitama (JP)

(72) Inventor: Tomonori Fukuchi, Saitama (JP)

(73) Assignee: RIKEN, Saitama (JP)

( * ) Notice: Subject to any disclaimer, the term of this patent is extended or adjusted under 35 U.S.C. 154(b) by 81 days.

(21) Appl. No.: 16/612,624

(22) PCT Filed: May 7, 2018

(86) PCT No.: PCT/JP2018/017657
§ 371 (c)(1),
(2) Date: Nov. 11, 2019

(87) PCT Pub. No.: WO2018/207739
PCT Pub. Date: Nov. 15, 2018

(65) Prior Publication Data
US 2020/0132867 A1 Apr. 30, 2020

(30) Foreign Application Priority Data
May 11, 2017 (JP) .............................. JP2017-094466

(51) Int. Cl.
*G01T 1/164* (2006.01)
*G01T 1/29* (2006.01)
(Continued)

(52) U.S. Cl.
CPC .......... *G01T 1/2985* (2013.01); *A61B 6/4258* (2013.01); *G01T 7/02* (2013.01)

(58) Field of Classification Search
CPC ........... G01T 1/2985; G01T 7/02; G01T 1/29; G01T 1/161; A61B 6/4258
See application file for complete search history.

(56) References Cited

U.S. PATENT DOCUMENTS

| | | | |
|---|---|---|---|
| 2014/0175293 A1 | 6/2014 | Fukuchi et al. | |
| 2016/0216385 A1* | 7/2016 | Moskal | G01T 1/1603 |
| 2018/0247432 A1* | 8/2018 | Gajos | G06T 11/006 |

FOREIGN PATENT DOCUMENTS

JP 5526435 B2 6/2014

OTHER PUBLICATIONS

Schueller et al., "Addressing the third gamma problem in PET," 2001 IEEE Nuclear Science Symposium Conference Record, pp. 1286-1289. (Year: 2002).*

(Continued)

*Primary Examiner* — Kiho Kim
(74) *Attorney, Agent, or Firm* — Osha Bergman Watanabe & Burton LLP

(57) ABSTRACT

A PET system with a positron lifetime measurement function includes: a first gamma ray detector configured to receive, from an imaging target containing a nuclide that goes into an excited state of a daughter nucleus by undergoing beta decay and that then, subsequently to emission of a positron resulting from the beta decay, emits a deexcitation gamma ray when transiting into a ground state of the daughter nucleus, three annihilation gamma rays resulting from the positron annihilating with an electron, the first gamma ray detector thereby detecting the three annihilation gamma rays; a second gamma ray detector configured to detect the deexcitation gamma ray; and a processor configured to derive, in three dimensions, a distribution state of the nuclide in the imaging target and to determine information on a positron lifetime in association with a derived distribution position.

8 Claims, 10 Drawing Sheets

(51) Int. Cl.
*A61B 6/00* (2006.01)
*G01T 7/02* (2006.01)

(56) References Cited

OTHER PUBLICATIONS

International Search Report issued in corresponding International Application No. PCT/JP2018/017657 dated Jul. 31, 2018 (4 pages).
Krzysztof Kacperski et al., "Three-Gamma Annihilations as a New Modality in PET"; IEEE Symposium Conference Record Nuclear Science 2004; pp. 3752-3756; Aug. 1, 2005 (5 pages).
Haruo Saito, "Positron lifetime measurement technique"; Japanese Positron Science Society; Positron Sciences, No. 2, pp. 21-27; Feb. 2014 (7 pages).
A. Andreyev et al., "Dual-isotope PET using positron-gamma emitters"; Physics in Medicine and Biology, No. 56, pp. 4539-4556; Jul. 1, 2011 (19 pages).
R. E. Bell et al., "Time Distribution of Positron Annihilation in Liquids and Solids"; Physical Review, vol. 90, No. 4, pp. 644-654; May 15, 1953 (11 pages).
Y. C. Jean et al., "Principles and Applications of Positron & Positronium Chemistry"; World Scientific, pp. 1-7; Apr. 2003 (5 pages).
A. M. Cooper et al., "Oxygen Quenching of Positron Lifetimes in Liquids"; The Journal of Chemical Physics, vol. 46 pp. 2441-2442; Mar. 1967 (3 pages).
Brian Hopkins et al., "Oxygen Quenching of Positronium in Silica Gels"; Physics Letter A, vol. 145, No. 2,3; pp. 141-145; Apr. 2, 1990 (5 pages).
Michael D. Harpen, "Positronium: Review of symmetry, conserved quantities and decay for the radiological physicist" Medical Physics, vol. 31, No. 1; pp. 57-61; Jan. 2004 (6 pages).
Krzysztof Kacperski et al., "Performance of three-photon PET imaging: Monte Carlo simulations"; Physics in Medicine and Biology, vol. 50, pp. 1-21; Jul. 11, 2005 (22 pages).

* cited by examiner

EXAMPLE OF TYPE A

EXAMPLE OF TYPE B

FIG.10

| EVENT NO. | 3 ANNIHILATION GAMMA RAYS | | | DEEXCITATION GAMMA RAY | |
|---|---|---|---|---|---|
| | DETECTION POSITIONS $P_{DET\gamma1} \sim P_{DET\gamma3}$ | DETECTION TIME POINTS $t_{DET\gamma1} \sim t_{DET\gamma3}$ | DETECTED ENERGIES $E_{DET\gamma1} \sim E_{DET\gamma3}$ | DETECTION TIME POINTS $t_{DET\gamma E}$ | DETECTED ENERGY $E_{DET\gamma E}$ |
| 1 | $P_{DET\gamma1}[1] \sim P_{DET\gamma3}[1]$ | $t_{DET\gamma1}[1] \sim t_{DET\gamma3}[1]$ | $E_{DET\gamma1}[1] \sim E_{DET\gamma3}[1]$ | $t_{DET\gamma E}[1]$ | $E_{DET\gamma E}[1]$ |
| 2 | $P_{DET\gamma1}[2] \sim P_{DET\gamma3}[2]$ | $t_{DET\gamma1}[2] \sim t_{DET\gamma3}[2]$ | $E_{DET\gamma1}[2] \sim E_{DET\gamma3}[2]$ | $t_{DET\gamma E}[2]$ | $E_{DET\gamma E}[2]$ |
| 3 | $P_{DET\gamma1}[3] \sim P_{DET\gamma3}[3]$ | $t_{DET\gamma1}[3] \sim t_{DET\gamma3}[3]$ | $E_{DET\gamma1}[3] \sim E_{DET\gamma3}[3]$ | $t_{DET\gamma E}[3]$ | $E_{DET\gamma E}[3]$ |
| --- | --- | --- | --- | --- | --- |
| n | $P_{DET\gamma1}[n] \sim P_{DET\gamma3}[n]$ | $t_{DET\gamma1}[n] \sim t_{DET\gamma3}[n]$ | $E_{DET\gamma1}[n] \sim E_{DET\gamma3}[n]$ | $t_{DET\gamma E}[n]$ | $E_{DET\gamma E}[n]$ |

| EVENT NO. | NUCLIDE POSITION NP | POSITRON LIFETIME LT |
|---|---|---|
| 1 | NP[1] | LT[1] |
| 2 | NP[2] | LT[2] |
| 3 | NP[3] | LT[3] |
| ⋮ | ⋮ | ⋮ |
| n | NP[n] | LT[n] |

PET SYSTEM WITH A POSITRON LIFETIME MEASUREMENT FUNCTION AND POSITRON LIFETIME MEASUREMENT METHOD IN A PET SYSTEM

TECHNICAL FIELD

The present invention relates to a PET system with a positron lifetime measurement function, and relates also to a positron lifetime measurement function in a PET system.

BACKGROUND ART

First Related Technology:

As one type of diagnostic equipment, positron emission tomography (PET) systems are in practical use. In a PET system, a positron-emitting nucleus is used as a tracer, and the distribution of the tracer is imaged by use of two gamma rays that are generated when a positron annihilates with an electron. The two gamma rays resulting from annihilation of a positron has a constant energy (511 keV) regardless of the nuclide, and this makes it impossible to discriminate the type of the positron-emitting nucleus that is the target of measurement. Thus, even if a plurality of kinds of tracer are administered to an imaging target simultaneously, it is generally impossible to image them in a discriminable manner. In recent years, PET systems that can image a plurality of kinds of tracer simultaneously in a manner that permits discrimination between different nuclides have been developed. Positron-emitting nuclides that can be used as tracers in PET divide into nuclides that emit a positron alone and nuclides that first emit a positron and then emit a deexcitation gamma ray. By using a nuclide of the latter type as a tracer and measuring not only the gamma rays resulting from annihilation but also the deexcitation gamma ray (with an energy intrinsic to the nuclide) emitted subsequently to the positron, it is possible to identify the nuclide (see Patent Document 1 and Non-Patent Document 1 identified below).

Second Related Technology:

On the other hand, positron annihilation lifetime spectroscopy (PALS) is a method for analyzing the structure of a substance by exploiting the fact that, when a positron annihilates with an electron, the lifetime of the positron varies depending on the environment around it. A positron emitted from a radioactive nuclide in a substance repeats collision with electrons around it and meanwhile gradually loses its momentum. When its momentum becomes nearly zero, the positron couples with an electron and undergoes annihilation. Immediately before the annihilation, the positron and the electron form positronium, which is a kind of molecular state where they are electrically bonded together. The decay lifetime of positronium is affected greatly by the electric field from electrons around it, and thus varies depending on the substance and its shape (molecular structure)—which determine the electron arrangement, temperature, and other factors. PALS exploits this variation of the lifetime to analyze a substance. The lifetime varies particularly greatly, for example, in the presence of holes in metal, and thus PALS is employed in analysis in the fields of material engineering, such as in analysis of semiconductor materials (see Non-Patent Documents 2 and 3 identified below). In recent years, studies have been made also on positrons emitted by use of an accelerator.

Third Related Technology:

A positron and an electron each have an intrinsic spin of ½. Accordingly, positronium can be either parapositronium, in which the intrinsic spins of the positron and the electron are identical, or orthopositronium, in which the intrinsic spins of the positron and the electron are opposite. Orthopositronium occurs only with a probability of 1% or less of the probability with which parapositronium occurs, but orthopositronium has a lifetime of 142 ns (nanoseconds) in vacuum, which is about 1000 times longer than the lifetime of parapositronium. It is also known that, while parapositronium decays into an even number of gamma rays (typically two gamma rays), orthopositronium decays into an odd number of gamma rays (typically three gamma rays). It has come to be known that, by examining the variation of the lifetime of orthopositronium, it is possible to conduct analysis not only in the fields of material engineering as mentioned above but also in the fields of life science, such as in analysis of oxygen concentration in liquid (see Patent Documents 4 and 5 identified below).

Fourth Related Technology:

As mentioned above, typically, while parapositronium undergoes annihilation by emitting two gamma rays, orthopositronium undergoes annihilation by emitting three gamma rays. In PET, it is common to perform imaging by using events involving decay into two gamma rays. This is because the probability with which a positron forms orthopositronium is 1% or less of the probability with which it forms parapositronium and thus, on annihilation of most positrons, two gamma rays are emitted. However, while in a case where two gamma rays are used, the position of annihilation is estimated as a straight line passing through two points of detection, in a case where three gamma rays are used, the position of annihilation can be estimated as a point by solving an equation of motion with respect to the momentum based on the energies of the three gamma rays. For this reason, in keeping with the increasingly high precision of modern radiation detectors (increasingly high energy resolution and position resolution, which affect the accuracy of position estimation), there has been proposed PET that uses three gamma rays (see Non-Patent Documents 6 and 7 identified below).

CITATION LIST

Patent Literature

Patent Document 1: Japanese Patent registered No. 5526435

Non-Patent Literature

Non-Patent Document 1: A. Andreyev, A. Celler, "Dual-isotope PET using positron-gamma emitters", Physics in Medical and Biology, 2011, 56, pp. 4539-4556

Non-Patent Document 2: R. B. Bell, R. L. Graham, "Time Distribution of Positron Annihilation in Liquids and Solids", Phys. Rev., 1953, 90, pp. 644-654

Non-Patent Document 3: "Principles and Applications of Positron and Positronium Chemistry", edited by: Y. C. Jean, P. E. Mallon, D. M. Schrader, World Scientific, 2003, ISBN:978-981-238-144-6

Non-Patent Document 4: A. M. Cooper, G. J. Laidlaw, B. G. Hogg, "Oxygen quenching of positron lifetimes in liquids", J. Chem. Phys., 1967, 46, 2441-2442

Non-Patent Document 5: B. Hopkins, T. W. Zerda, "Oxygen quenching of positronium in silica gels", Phys. Lett., 1990, A45, 141-145

Non-Patent Document 6: M. D. Harpen, "Positronium: Review of symmetry, conserved quantities and decay for the radiological physicist", Medical Physics, 2004, 31(1), pp. 57-61

Non-Patent Document 7: K. Kacperski, M. N. Spyrou, "Performance of three-photon PET imaging: Monte Carlo simulations", Phys. Med. Biol., 2005, 50, pp. 5679-5696

SUMMARY OF INVENTION

Technical Problem

PET is useful in various kinds of diagnosis, such as in cancer screening; however, conventional PET only provides information on the distribution of a tracer. If, for the sake of discussion, PET can provide information on the lifetime of positrons in association with information on the distribution of a tracer, it will then be possible to obtain not only information on the distribution of the tracer but also detailed information on the environment (oxygen concentration, structure, and the like) around each distribution position of the tracer. This is expected to bring about new analysis methods in the fields of life science and the like.

Against the background discussed above, an object of the present invention is to provide a PET system with a positron lifetime measurement function, and a positron lifetime measurement method in a PET system, that contribute to more detailed analysis of imaging targets.

Solution to Problem

According to one aspect of the present invention, a PET system with a positron lifetime measurement function includes: a first gamma ray detector configured to receive, from an imaging target containing a nuclide that goes into an excited state of a daughter nucleus by undergoing beta decay and that then, subsequently to emission of a positron resulting from the beta decay, emits a deexcitation gamma ray when transiting into a ground state of the daughter nucleus, three annihilation gamma rays resulting from the positron annihilating with an electron, thereby to detect the three annihilation gamma rays; a second gamma ray detector configured to detect the deexcitation gamma ray; and a processor configured to derive, in three dimensions, a distribution state of the nuclide in the imaging target, and to determine information on a positron lifetime in association with a derived distribution position, based on the detected energy and the detection position of each of the annihilation gamma rays as detected by the first gamma ray detector as well as the detection time point of the annihilation gamma rays as detected by the first gamma ray detector and the detection time point of the deexcitation gamma ray as detected by the second gamma ray detector.

With this system, it is possible to know the distribution state of the nuclide and also obtain information on the positron lifetime at each distribution position of the nuclide. This is expected to make it possible to grasp properties (oxygen concentration, molecular structure, etc.) at each position in the imaging target in a non-invasive manner. This is expected to bring about new analysis methods in the field of life science and the like.

According to another aspect of the present invention, a method of measuring the lifetime of a positron in a PET system including a first gamma ray detector configured to receive, from an imaging target containing a nuclide that goes into an excited state of a daughter nucleus by undergoing beta decay and that then, subsequently to emission of a positron resulting from the beta decay, emits a deexcitation gamma ray when transiting into a ground state of the daughter nucleus, three annihilation gamma rays resulting from the positron annihilating with an electron, thereby to detect the three annihilation gamma rays, and a second gamma ray detector configured to detect the deexcitation gamma ray includes deriving, in three dimensions, a distribution state of the nuclide in the imaging target and determining information on a positron lifetime in association with a derived distribution position, based on the detected energy and the detection position of each of the annihilation gamma rays as detected by the first gamma ray detector as well as the detection time point of the annihilation gamma rays as detected by the first gamma ray detector and the detection time point of the deexcitation gamma ray as detected by the second gamma ray detector.

With this system, it is possible to know the distribution state of the nuclide and also obtain information on the positron lifetime at each distribution position of the nuclide. This is expected to make it possible to grasp properties (oxygen concentration, molecular structure, etc.) at each position in the imaging target in a non-invasive manner. This is expected to bring about new analysis methods in the field of life science and the like.

Advantageous Effects of Invention

According to the present invention, it is possible to provided a PET system with a positron lifetime measurement function, and a positron lifetime measurement method in a PET system, that contribute to more detailed analysis of imaging targets.

BRIEF DESCRIPTION OF DRAWINGS

FIG. 10 is a diagram showing how a plurality of sets of 4γ event data are recorded;

DESCRIPTION OF EMBODIMENTS

Hereinafter, examples embodying the present invention will be described specifically with reference to the accompanying drawings. Among the diagrams referred to, the same parts are identified by the same reference signs, and in principle no overlapping description of the same parts will be repeated. In the present description, for the sake of simple description, symbols and other designations referring to information, signals, physical quantities, components, and the like are occasionally used with the names of the corresponding information, signals, physical quantities, components, and the like omitted or abbreviated.

Figure 1:
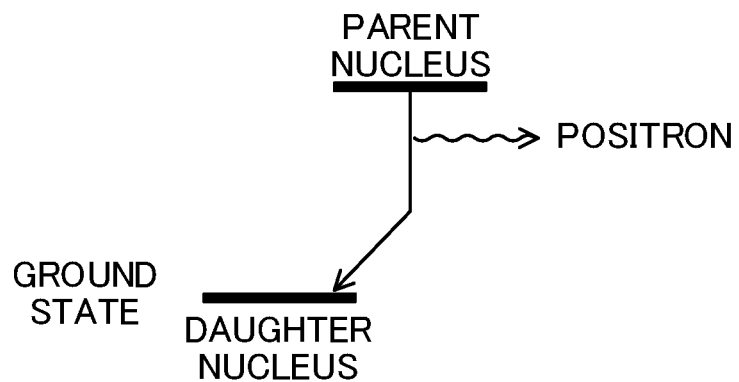
FIG. 1 is a diagram showing a mode of type A radioactive decay.
Figure 2:
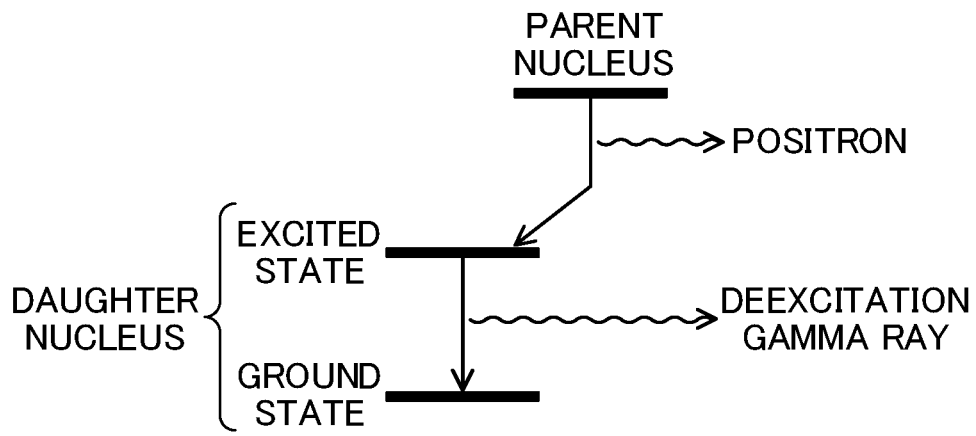
FIG. 2 is a diagram showing a mode of type B radioactive decay.

First, with reference to FIGS. 1 and 2, a description will be given of two modes of radioactive decay of a positron-emitting nucleus (a nuclide that emits a positron through radioactive decay). FIG. 1 shows a type A mode of radioactive decay, and FIG. 2 shows a type B mode of radioactive decay. Positron-emitting nuclei that undergo radioactive decay in the type A and type B modes are referred to as type A and type B nuclides respectively. With respect to a given positron-emitting nucleus, the nuclide before beta decay is referred to as the parent nucleus, and the nuclide after beta decay is referred to as the daughter nucleus.

As shown in FIG. 1, in a type A nuclide, the parent nucleus undergoes beta decay to transit to the daughter nucleus in the ground state while emitting a positron. That is, through beta decay, a type A nuclide transits from the energy level of the parent nucleus directly to the energy level of the daughter nucleus in the ground state, and during the transition, a positron is emitted.

As shown in FIG. 2, in a type B nuclide, the parent nucleus undergoes beta decay to transit to the daughter nucleus in an excited state while emitting a positron, and subsequently this, that is, the daughter nucleus in the excited state, undergoes gamma decay by emitting a deexcitation gamma ray with an energy intrinsic to the type B nuclide to transit to the daughter nucleus in the ground state. The energy difference of the daughter nucleus of the type B nuclide between the excited and ground states is the energy of the deexcitation gamma ray. In a type B nuclide, the time point at which the deexcitation gamma ray is emitted is dictated by a quantum-mechanical probability that depends on the structure of the nucleus. An index of the lifetime from the excited state to the ground state of the daughter nucleus is given as a half-life. In a PET system according to an embodiment of the present invention, a type B positron-emitting nucleus is used.

Figure 3:
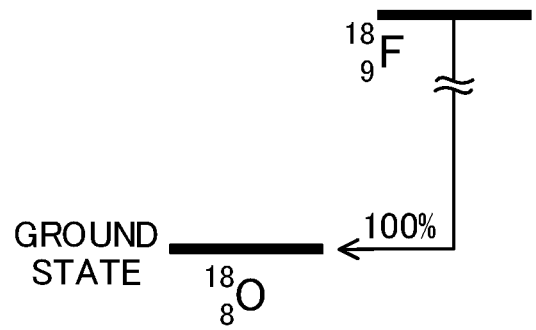
FIG. 3 is a diagram showing a specific example of type A radioactive decay.

FIG. 3 shows one example of type A radioactive decay. When $^{18}$F, which is the parent nucleus of a type A nuclide, undergoes beta decay, it transits to the ground state of $^{18}$O, which is the daughter nucleus, with a probability of 100%. During the beta decay, a positron is emitted.

Figure 4:
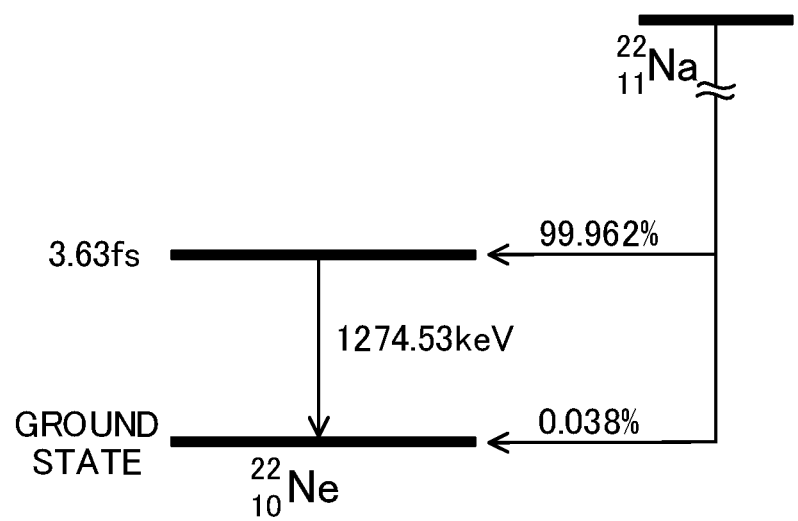
FIG. 4 is a diagram showing a specific example of type B radioactive decay.

FIG. 4 shows one example of type B radioactive decay. $^{22}$Na, which is the parent nucleus of a type B nuclide, goes through an excited state of $^{22}$Ne, which is the daughter nucleus, with a probability of about 99.96% before transiting to the ground state of $^{22}$Ne. Meanwhile, through gamma decay, the excited state of $^{22}$Ne transits to the ground state of $^{22}$Ne with a half-life of about 3.63 fs (femtoseconds). During this transition, a deexcitation gamma ray with an energy of 1275 keV (kiloelectronvolts) is emitted. During the beta decay that brings about the transition from $^{22}$Na to the excited state of $^{22}$Ne, a positron is emitted. It should be noted that a type B nuclide can, in the process of transiting from the parent nucleus to the ground state of the daughter nucleus, go through a plurality of excited states of the daughter nucleus, meanwhile emitting a plurality of deexcitation gamma rays.

As mentioned earlier, a positron emitted from a positron-emitting nucleus in a substance repeats collision with electrons around it and meanwhile gradually loses its momentum. When its momentum becomes nearly zero, the positron couples with an electron and undergoes annihilation. Immediately before the annihilation, the positron and the electron form positronium, which is a kind of molecular state where they are electrically bonded together. Positronium can be either parapositronium, in which the intrinsic spins of the positron and the electron are identical, or orthopositronium, in which the intrinsic spins of the positron and the electron are opposite. Orthopositronium occurs only with a probability of 1% or less of the probability with which parapositronium occurs, but orthopositronium has a lifetime about 1000 times longer than the lifetime of parapositronium. It is also known that, while parapositronium decays into an even number of gamma rays (typically two gamma rays), orthopositronium decays into an odd number of gamma rays (typically three gamma rays). A gamma ray that is emitted when a positron and an electron annihilate is referred to as an annihilation gamma ray.

Figure 5:
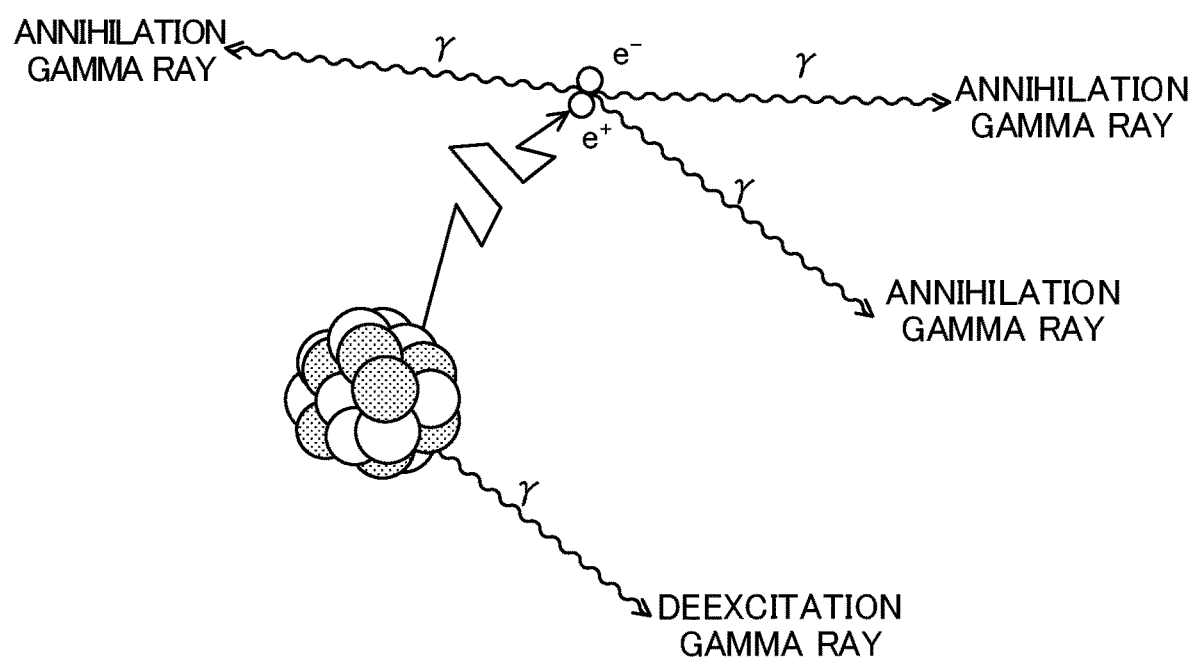
FIG. 5 is a diagram showing how emission of a positron from a positron-emitting nucleus is followed by emission of a deexcitation gamma ray while annihilation of the positron generates three annihilation gamma rays.

As shown in FIG. 5, when a type B positron-emitting nucleus undergoes beta decay, a positron is emitted, and subsequently a deexcitation gamma ray is emitted. If the emitted positron forms orthopositronium with an electron around it, when they annihilate, three annihilation gamma rays are emitted. In the following description, it is assumed that, whenever simply three annihilation gamma rays are mentioned, they refer to the three annihilation gamma rays that are emitted when a positron and an electron forming orthopositronium annihilate. The three annihilation gamma rays have a total energy of 1022 keV (kiloelectronvolts), which corresponds to the sum of the rest masses of a positron and an electron.

Figure 6:
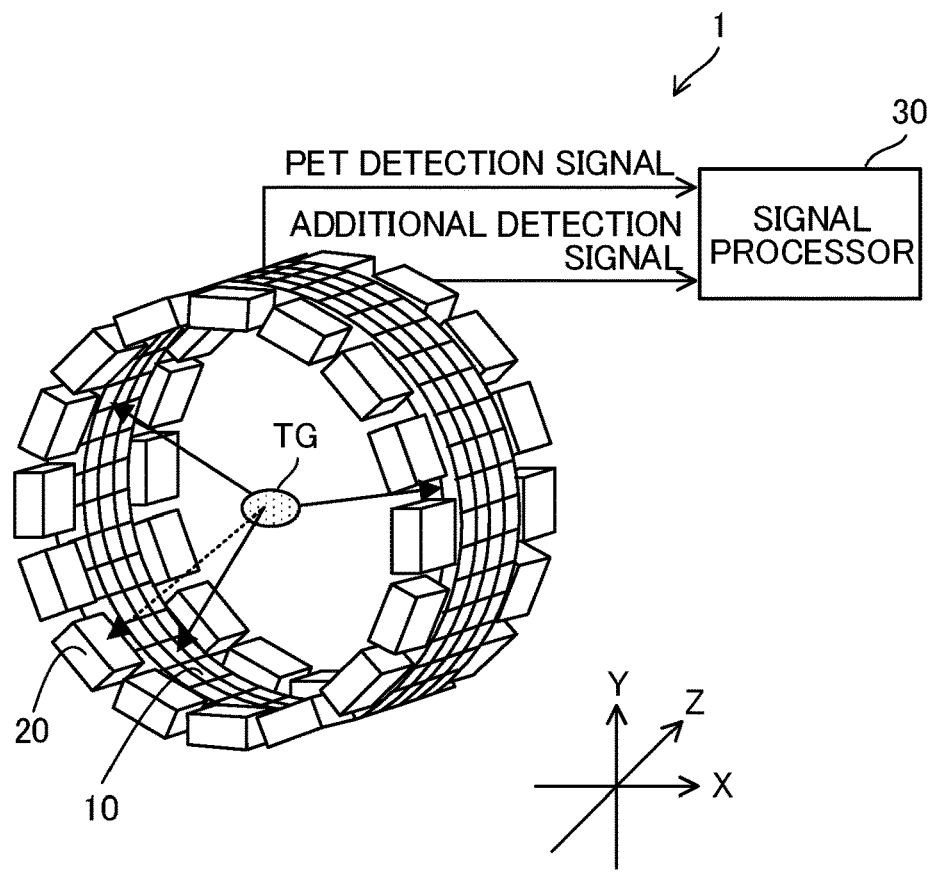
FIG. 6 is an outline configuration diagram of a PET system according to an embodiment of the present invention.

FIG. 6 is an outline configuration diagram of a PET system 1 according to an embodiment. The PET system 1 includes a PET detector 10, a deexcitation gamma ray detector 20, and a signal processor 30. The reference symbol "TG" indicates an imaging target in the PET system 1. The imaging target TG is an object that contains a type B positron-emitting nucleus, and a living body can be taken as the imaging target TG. The type B positron-emitting nucleus is distributed within the imaging target TG.

In real space, a three-dimensional space is defined by X-, Y-, and Z-axes that are perpendicular to each other, and is referred to as XYZ space. The X-axis, Y-axis, and Z-axis components of a given position are represented by x, y, and z respectively, and the position of a given point in XYZ space is represented by (x, y, z).

As mentioned previously, in the PET system 1 according to an embodiment of the present invention, a type B positron-emitting nucleus is used. Then, through detection of a total of three annihilation gamma rays emitted during annihilation of orthopositronium and detection of a deexcitation gamma ray, the distribution of the positron-emitting nucleus is estimated as well as information on the lifetime of the positron is acquired. The lifetime of parapositronium, which is commonly used in conventional PET systems, is of the order of 100 ps (picoseconds), and is thus difficult to measure in existing PET systems with their time resolution in comparison with the lifetime. As a solution, in the embodiment, the lifetime of orthopositronium is measured on such an order (about 100 ns (nanoseconds)) as to be relatively easy to measure. Now, the constituent elements of the PET system 1 will be described.

[PET Detector]

Figure 7:
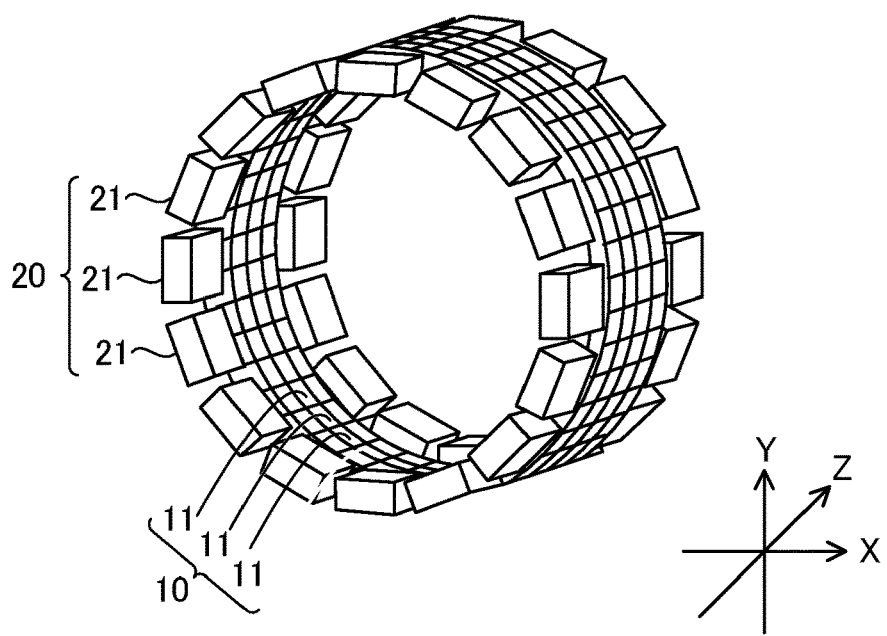
FIG. 7 is a diagram illustrating the PET detector and the deexcitation gamma ray detector in FIG. 6 each being composed of a plurality of gamma ray detectors.

The PET detector 10 is arranged in such a position as to surround the imaging target TG so as to be able to receive the annihilation gamma rays (typically, three annihilation gamma rays) that are emitted when a positron emitted from a positron-emitting nucleus in the imaging target TG annihilates with an electron around the positron. Thus, the PET detector 10 receives gamma rays including annihilation gamma rays and thereby detects those gamma rays. Specifically, as shown in FIG. 7, like a PET detector on a conventional PET system, the PET detector 10 is composed of a plurality of gamma ray detectors 11 arrayed in a ring. That is, the PET detector 10 is formed by a plurality of gamma ray detectors 11 that are arranged on, so as to be distributed across, a curved face that defines a generally cylindrical surface. The space surrounded by the detector 10 where imaging is possible is generally called a FOV (field of view), and inside the FOV, the imaging target TG is arranged. In FIGS. 6 and 7, the axis of the FOV, which defines a cylindrical surface, is parallel to the Z axis. For the sake of simple illustration, in FIG. 7, only some of the gamma ray detectors constituting the PET detector 10 are identified by the reference symbol "11".

The gamma ray detectors 11 are each a radiation detector that can detect gamma rays. When a gamma ray emanating from inside the FOV is incident on a gamma ray detector 11, it outputs a PET detection signal commensurate with the interaction between the incident gamma ray and the gamma ray detector 11 itself. Each gamma ray detector 11 can detect the position of the interaction between a gamma ray and the gamma ray detector 11 and the energy of the incident gamma ray. The output signal of the gamma ray detector 11 includes position information, which indicates the detection position, and energy information, which indicates the detected energy. The position indicated by the position information included in the PET detection signal is obtained owing to the PET detector being segmentalized, and includes the X-axis, Y-axis, and Z-axis components of the gamma ray detection position in units of the size of the segmentalized detectors.

Since the PET detector 10 is composed of a plurality of gamma ray detectors 11, the PET detector 10 as a whole operates in the following manner: when a gamma ray emanating from inside the FOV is incident on any of the gamma ray detector 11, the detection position of the incident gamma ray (that is, the position of whichever of the detectors constituting the detector 10 has interacted with the incident gamma ray) and the energy of the incident gamma ray are detected, and a PET detection signal including position information indicating the detection position and energy information indicating the detected energy is output. When more than one of the gamma ray detectors 11 are each struck by and detect a gamma ray, a plurality of PET detection signals corresponding to their respective detection are output from the PET detector 10.

[Deexcitation Gamma Ray Detector]

The deexcitation gamma ray detector 20 is arranged in such a position as to surround the imaging target TG so as to be able to receive a deexcitation gamma ray emitted from a positron-emitting nucleus in the imaging target TG. Thus, the deexcitation gamma ray detector 20 receives gamma rays including deexcitation gamma rays and thereby detects those gamma rays. The deexcitation gamma ray detector 20 is arranged in any position inside the space excluding where the PET detector 10 is arranged. Specifically, for example, as shown in FIG. 7, a plurality of gamma ray detectors 21 are arranged on, so as to be distributed across, a cylindrical surface that is coaxial with the cylindrical surface defined by the arrangement face of the plurality of gamma ray detectors 11. The plurality of gamma ray detectors 21 are arranged in a ring, and are located on both sides of the array of the gamma ray detectors 11 along the axial direction of the above-mentioned cylindrical surface. For the sake of simple illustration, in FIG. 7, only some of the gamma ray detectors constituting the deexcitation gamma ray detector 20 are identified by the reference symbol "21".

The gamma ray detectors 21 are each a radiation detector that can detect gamma rays. When a gamma ray emanating from inside the FOV is incident on a gamma ray detector 21, it outputs an additional detection signal commensurate with the interaction between the incident gamma ray and the gamma ray detector 21 itself. Each gamma ray detector 21 can detect the energy of the incident gamma ray. The output signal of the gamma ray detector 21 includes energy information, which indicates the detected energy. Unlike the PET detector 10, the gamma ray detectors 21 do not need to be position-sensitive.

Since the deexcitation gamma ray detector 20 is composed of a plurality of gamma ray detectors 21, the deexcitation gamma ray detector 20 as a whole operates in the following manner: when a gamma ray is incident on and detected by any of the gamma ray detectors 21, the energy of the incident gamma ray is detected, and a signal including energy information indicating the detected energy is output. Here, a gamma ray detection signal as the output signal of the deexcitation gamma ray detector 20 is referred to as an additional detection signal. Of gamma ray detection signals as the output signal of the deexcitation gamma ray detector 20, any occurring on detection of a deexcitation gamma ray in the deexcitation gamma ray detector 20 is in particular referred to as a deexcitation gamma ray detection signal.

For example, the gamma ray detectors 11 and 21 can be configured as semiconductor detectors using Ge (germanium). In that case, the gamma ray detectors 11 and 21 can detect the energy of a gamma ray with an energy resolution of 0.2 to 0.5%. Instead, semiconductor detectors using any other semiconductor material (for example, Si, CdTe, or CdZnTe) than Ge may be used as the gamma ray detectors 11 and 21. Or scintillation detectors may be used to build the gamma ray detectors 11 and 21.

The number of gamma ray detector 21 that constitute the deexcitation gamma ray detector 20 is determined with consideration given to the size of the gamma ray detector 21 and the dose of gamma rays to be detected by the gamma ray detector 21. The number can be one.

[Signal Processor]

The signal processor 30 performs, among others, reconstruction of a distribution image of a target nuclide contained in the imaging target TG, based on the PET detection signal output from the PET detector 10 and the additional detection signal output from the deexcitation gamma ray detector 20. The target nuclide refers to the nuclide that is contained in the imaging target TG and that is the target of imaging of distribution. In the following description, unless otherwise stated, it is assumed that the imaging target TG contains only one kind of type B positron-emitting nucleus, and this type B positron-emitting nucleus is the target nuclide. A distribution image of the target nuclide is a three-dimensional distribution image that shows three-dimensional distribution of the target nuclide in XYZ space. A drug can be labeled with a type B positron-emitting nucleus; thus, the imaging target TG can contain a type B positron-emitting nucleus in a form mixed in a drug. In that case, a distribution image of the target nuclide can be said to be a distribution image of the drug (probe) labeled with the type B positron-emitting nucleus.

—Three-Gamma (3γ) Check Process—

Figure 8:
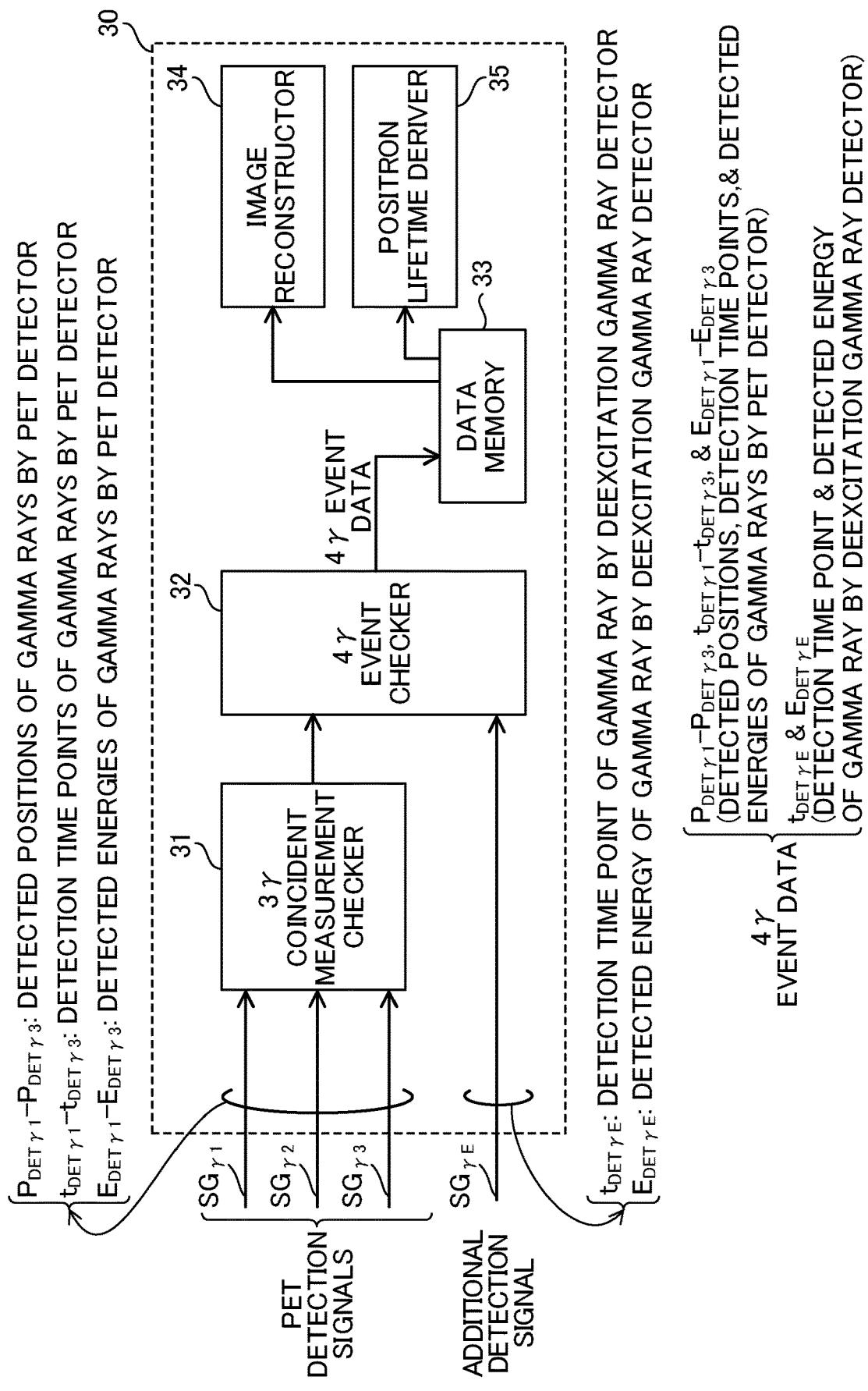
FIG. 8 is an internal block diagram of the signal processor in FIG. 6.

As shown in FIG. 8, the signal processor 30 includes a three-gamma (3γ) coincident measurement checker 31. When fed with PET detection signals indicating that three gamma rays have been detected in the PET detector 10, the 3γ coincident measurement checker 31 performs a 3γ check process to check whether or not the PET detection signals indicate coincident measurement of the three gamma rays.

Specifically, when the signal processor 30 (here, the 3γ coincident measurement checker 31) is fed with three PET detection signals $SG_{\gamma 1}$, $SG_{\gamma 2}$, and $SG_{\gamma 3}$ indicating that three gamma rays have been detected at three mutually different positions, respectively, in the PET detector 10, then the 3γ coincident measurement checker 31 identifies the detection time points $t_{DET\gamma 1}$, $t_{DET\gamma 2}$, and $t_{DET\gamma 3}$ of the three gamma rays based on the input time points of the PET detection signals $SG_{\gamma 1}$, $SG_{\gamma 2}$, and $SG_{\gamma 3}$, and also identifies the detected energies $E_{DET\gamma 1}$, $E_{DET\gamma 2}$, and $E_{DET\gamma 3}$ of the three gamma rays based on the energy information included in the PET detection signals $SG_{\gamma 1}$, $SG_{\gamma 2}$, and $SG_{\gamma 3}$.

Here, the detection time point $t_{DET\gamma 1}$ of the gamma ray based on the PET detection signal $SG_{\gamma 1}$ refers to the time point at which that gamma ray interacted with the PET detector 10. Similar description applies to the detection time points $t_{DET\gamma 2}$ and $t_{DET\gamma 3}$. In practice, however, the time points at which the PET detection signals $SG_{\gamma 1}$ to $SG_{\gamma 3}$ are fed to the signal processor 30 can be taken as the detection time points $t_{DET\gamma 1}$ to $t_{DET\gamma 3}$ (this will be discussed again later). Although the PET detection signals $SG_{\gamma 1}$, $SG_{\gamma 2}$, and $SG_{\gamma 3}$ also include position information indicating the detected positions $P_{DET\gamma 1}$ to $P_{DET\gamma 3}$ of the gamma rays as detected by the PET detector 10, the position information is not used in the 3γ check process.

If, in the 3γ check process, the detection time points $t_{DET\gamma 1}$, $t_{DET\gamma 2}$, and $t_{DET\gamma 3}$ coincide and in addition the sum of the detected energies $E_{DET\gamma 1}$, $E_{DET\gamma 2}$, and $E_{DET\gamma 3}$ equals 1022 keV, the 3γ coincident measurement checker 31 judges that three annihilation gamma rays were measured coincidentally; otherwise, the 3γ coincident measurement checker 31 does not judge that three annihilation gamma rays were measured coincidentally.

Considering, however, that a judgment on the sum of the detected energies is generally performed off-line, the 3γ check process can usually proceed as follows: if the $t_{DET\gamma 1}$, $t_{DET\gamma 2}$, and $t_{DET\gamma 3}$ coincide, it is judged that there is a possibility of three annihilation gamma rays having been measured coincidentally, while otherwise it is judged that there is no possibility of three annihilation gamma rays having been measured coincidentally; thereafter, off-line, the detected energies $E_{DET\gamma 1}$, $E_{DET\gamma 2}$, and $E_{DET\gamma 3}$ of the three annihilation gamma rays that have been judged to be likely to have been measured coincidentally are referred to judge, if the sum of the detected energies $E_{DET\gamma 1}$, $E_{DET\gamma 2}$, and $E_{DET\gamma 3}$ equals 1022 keV, that the three annihilation gamma rays were measured coincidentally.

Here, the concept of coincidence allows for a predetermined width of time: if the maximum difference among the detection time points $t_{DET\gamma 1}$ to $t_{DET\gamma 3}$ is equal to or less than a predetermined value determined with consideration given to the time resolution of the system that identifies the detection time points $t_{DET\gamma 1}$ to $t_{DET\gamma 3}$, these detection time points $t_{DET\gamma 1}$ to $t_{DET\gamma 3}$ are judged to coincide; otherwise, the detection time points $t_{DET\gamma 1}$ to $t_{DET\gamma 3}$ are not judged to coincide.

Each instance of one or more gamma rays being detected by at least either of the PET detector 10 and the deexcitation gamma ray detector 20 is referred to as an event. Of all events in which an annihilation gamma ray is detected, most are positron annihilation events, that is, events in which two annihilation gamma rays of 511 keV are generated. Thus, events in which three gamma rays are measured coincidentally in the PET detector 10 include many false events such as events resulting from accidental coincident measurement and events resulting from scattering of a deexcitation gamma ray (events in which the phenomenon of a deexcitation gamma ray striking and being scattered by the PET detector 10 is recognized as part of detection of three gamma rays). However, by judging whether the sum of the energies of three gamma rays amounts to 1022 keV as a process prior to image reconstruction, it is possible to exclude most false events.

Here, to say "the sum of the energies of three gamma rays amounts to 1022 keV" is to say "the sum of the detected energies $E_{DET\gamma 1}$, $E_{DET\gamma 2}$, and $E_{DET\gamma 3}$ equals 1022 keV". In the expression "the sum of the detected energies $E_{DET\gamma 1}$, $E_{DET\gamma 2}$, and $E_{DET\gamma 3}$ equals 1022 keV", the concept of equality allows for a predetermined width: if the sum of the detected energies $E_{DET\gamma 1}$ to $E_{DET\gamma 3}$ falls, for example, within the range of energy equal to or more than $(1022-\Delta E_1)$ keV but equal to or less than $(1022+\Delta E_1)$ keV, the sum of the detected energies $E_{DET\gamma 1}$, $E_{DET\gamma 2}$, and $E_{DET\gamma 3}$ is judged to equal 1022 keV; otherwise the sum of the detected energies $E_{DET\gamma 1}$, $E_{DET\gamma 2}$, and $E_{DET\gamma 3}$ is judged not to equal 1022 keV. $\Delta E_1$ represents a predetermined energy determined with consideration given to the energy resolution of the PET detector 10.

Even when the above check is performed, if an annihilation gamma ray in a positron annihilation event, that is, an event in which two annihilation gamma rays of 511 keV are generated, is scattered by one of the gamma ray detectors 11 constituting the PET detector 10 and all the rest of the energy of the scattered annihilation gamma ray is absorbed by another of the gamma ray detectors 11 constituting the PET detector 10, this can be erroneously judged to be a 3γ event (an event in which three annihilation gamma rays are detected coincidentally). When three gamma rays are emitted as a result of annihilation, every one of the three gamma rays has an energy of 511 keV or less and rarely has an energy of exactly 511 keV. Accordingly, it is possible to exclude most such erroneously judged events by posing, in addition to the condition that the sum of the energy of three gamma rays equals 1022 keV, the condition that every one of three gamma rays has an energy less than 511 keV (that is, by not judging that three annihilation gamma rays were measured coincidentally unless the two conditions are both met).

—Four-Gamma (4γ) Check Process—

The signal processor 30 further includes a four-gamma (4γ) event checker 32. Based on the check result from the 3γ coincident measurement checker 31 and the additional detection signal $SG\gamma_E$ from the deexcitation gamma ray detector 20, the 4γ event checker 32 performs a 4γ check process to check whether or not a 4γ event has occurred. A 4γ event denotes an event that meets a specific condition. Specifically, a 4γ event denotes an event in which a deexcitation gamma ray is detected in the deexcitation gamma ray detector 20 and in addition, within a predetermined time $T_{WINDOW}$ of the detection time point of the deexcitation gamma ray, three annihilation gamma rays are measured coincidentally.

Ideally, it is preferable that only a true 4γ event, that is, a 4γ event that occurs based on a deexcitation gamma ray emitted from a single positron-emitting nucleus and the three annihilation gamma rays that are generated when a positron emitted from the single positron-emitting nucleus undergoes annihilation, be judged to be a 4γ event.

If the predetermined time $T_{WINDOW}$ is too long, a false 4γ event in which a deexcitation gamma ray emitted from a given positron-emitting nucleus and the three annihilation gamma rays generated when a positron emitted from another positron-emitting nucleus undergoes annihilation are accidentally measured coincidentally can be erroneously recognized as a 4γ event. Such events appear as noise in images, but can be compensated for by a method such as simultaneous delay measurement similar to that in existing PET imaging. Even so, higher compensation accuracy requires as few false 4γ events as possible. On the other hand, if the predetermined time $T_{WINDOW}$ is too short, failed recognition can lead to a true 4γ event not being recognized as a 4γ event. To minimize erroneous and failed recognition, it is preferable that the predetermined time $T_{WINDOW}$ be set based on the half-life of orthopositronium in vacuum, in which it has the longest half-life, or based on the maximum value of the half-life that the orthopositronium is presumed to have within the imaging target TG.

Specifically, when the signal processor 30 (here, the 4γ event checker 32) is fed with an additional detection signal $SG\gamma_E$ indicating that a gamma ray has been detected in the deexcitation gamma ray detector 20, the 4γ event checker 32 identifies the detection time point $t_{DET\gamma E}$ of that gamma ray based on the input time point of the additional detection signal $SG\gamma_E$, and also identifies the detected energy $E_{DET\gamma E}$ of that gamma ray based on the energy information included in the additional detection signal $SG\gamma_E$. Here, the detection time point $t_{DET\gamma E}$ of the gamma ray based on the additional detection signal $SG\gamma_E$ refers to the time point at which the gamma ray in question interacted with the deexcitation gamma ray detector 20.

A supplementary description will now be given of the detection time points $t_{DET\gamma 1}$ to $t_{DET\gamma 3}$ and $t_{DET\gamma E}$. In practical terms, the time points at which the PET detection signals $SG_{\gamma 1}$ to $SG_{\gamma 3}$ are fed to the signal processor 30 can be dealt with as the detection time points $t_{DET\gamma 1}$ to $t_{DET\gamma 3}$, and the time point at which the additional detection signal $SG\gamma_E$ is fed to the signal processor 30 can be dealt with as the detection time point $t_{DET\gamma E}$. A predetermined response time is required after a gamma ray interacts with a gamma ray detector (11, 21) until a signal (PET detection signal, additional detection signal) resulting from the interaction is fed to the signal processor 30. To make the response time equal among a plurality of gamma ray detectors (11, 21), as necessary, a signal delay circuit is inserted between any one or more of the plurality of gamma ray detectors and the signal processor 30. What poses a problem in the processing in the signal processor 30 is differences among detection time points, and thus if the response time is equal among the plurality of gamma ray detectors (11, 21), no problem arises.

In the 4γ check process, the 4γ event checker 32 recognizes as a 4γ event only such an event as meets both of the first and second 4γ check conditions described below. Here, the energy of a deexcitation gamma ray from a positron-emitting nucleus distributed in the imaging target TG is represented by $E_{\gamma E}$. The energy $E_{\gamma E}$ is known to the signal processor 30.

The first 4γ check condition is that the detected energy $E_{DET\gamma E}$ equals the energy $E_{\gamma E}$ of a deexcitation gamma ray.

Again, the concept of equality here allows for a predetermined width: for example, if the detected energy $E_{DET\gamma E}$ falls within the range equal to or more than $(E_{\gamma E}-\Delta E_2)$ but equal to or less than $(E_{\gamma E}+\Delta E_2)$ keV, the detected energy $E_{DET\gamma E}$ is judged to be equal to the energy $E_{\gamma E}$ of the deexcitation gamma ray; otherwise, the detected energy $E_{DET\gamma E}$ is judged not to be equal to the energy $E_{\gamma E}$ of the deexcitation gamma ray. Here, $\Delta E_2$ represents a predetermined energy determined with consideration given to the energy resolution of the deexcitation gamma ray detector 20.

When the first 4γ check condition is met, the gamma ray corresponding to the detected energy $E_{DET\gamma E}$ and detected by the deexcitation gamma ray detector 20 is judged to be a deexcitation gamma ray.

The second 4γ check condition is that three annihilation gamma rays are measured coincidentally within the predetermined time $T_{WINDOW}$ of the detection time point $t_{DET\gamma E}$ of a gamma ray as detected by the deexcitation gamma ray detector 20. Only when the first 4γ check condition is met is it necessary to check whether the second 4γ check condition is met.

That is, if, under the assumption that the first 4γ check condition is met, it is judged that the three annihilation gamma rays corresponding to the detection time points $t_{DET\gamma 1}$ to $t_{DET\gamma 3}$ have been measured coincidentally in the 3γ check process; in addition if the detection time point of the three annihilation gamma rays based on the detection time points $t_{DET\gamma 1}$ to $t_{DET\gamma 3}$ occurs after the detection time point of the deexcitation gamma ray corresponding to the detection time point $t_{DET\gamma E}$; and in addition the time lag between the detection time point of the deexcitation gamma ray and the detection time point of the three annihilation gamma rays is within the predetermined time $T_{WINDOW}$, only then the second 4γ check condition is met; otherwise, the second 4γ check condition is not met.

The detection time point of the three annihilation gamma rays based on the detection time points $t_{DET\gamma 1}$ to $t_{DET\gamma 3}$ may be the average time point of the detection time points $t_{DET\gamma 1}$ to $t_{DET\gamma 3}$, or may be one of the detection time points $t_{DET\gamma 1}$ to $t_{DET\gamma 3}$.

On judging that the event corresponding to the PET detection signals $SG_{\gamma 1}$ to $SG_{\gamma 3}$ and the additional detection signal $SG\gamma_E$ is a 4γ event, the 4γ event checker 32 creates, as 4γ event data, data based on the PET detection signals $SG_{\gamma 1}$ to $SG_{\gamma 3}$ and the additional detection signal $SG\gamma_E$, and stores the created 4γ event data on a data memory 33 provided in the signal processor 30.

The 4γ event data based on the PET detection signals $SG_{\gamma 1}$ to $SG_{\gamma 3}$ and the additional detection signal $SG\gamma_E$ includes the detection time points $t_{DET\gamma 1}$ to $t_{DET\gamma 3}$ and $t_{DET\gamma E}$ and the detected energies $E_{DET\gamma 1}$ to $E_{DET\gamma 3}$ and $E_{DET\gamma E}$ mentioned above, and further includes detection positions $P_{DET\gamma 1}$ to $P_{DET\gamma 3}$ indicated by the position information included in the PET detection signals $SG_{\gamma 1}$ to $SG_{\gamma 3}$.

With respect to a given 4γ event, the detection time points $t_{DET\gamma 1}$ to $t_{DET\gamma 3}$ represent the detection time points of the three annihilation gamma rays in the 4γ event and the detection time point $t_{DET\gamma E}$ represents the detection time point of the deexcitation gamma ray in the 4γ event;

the detected energies $E_{DET\gamma 1}$ to $E_{DET\gamma 3}$ represent the detected energies of the three annihilation gamma rays in the 4γ event and the detected energy $E_{DET\gamma E}$ represents the detected energy of the deexcitation gamma ray in the 4γ event; and the detection positions $P_{DET\gamma 1}$ to $P_{DET\gamma 3}$ represent the detection positions of the three annihilation gamma rays in the 4γ event (the positions of the interaction between the annihilation gamma rays and the PET detector 10).

By recording, with a common time stamp, the data based on the PET detection signals $SG_{\gamma 1}$ to $SG_{\gamma 3}$ and the additional detection signal $SG\gamma_E$, it is possible to record 4γ event data including recording of the detection time points $t_{DET\gamma 1}$ to $t_{DET\gamma 3}$ and $t_{DET\gamma E}$, and check for coincident measurement off-line.

In the configuration shown in FIG. 8, the 3γ coincident measurement checker 31 and the 4γ event checker 32 are provided as separate blocks; instead, they may be integrated into a single block so that this single block performs the 3γ and 4γ check processes described above.

Figure 9:
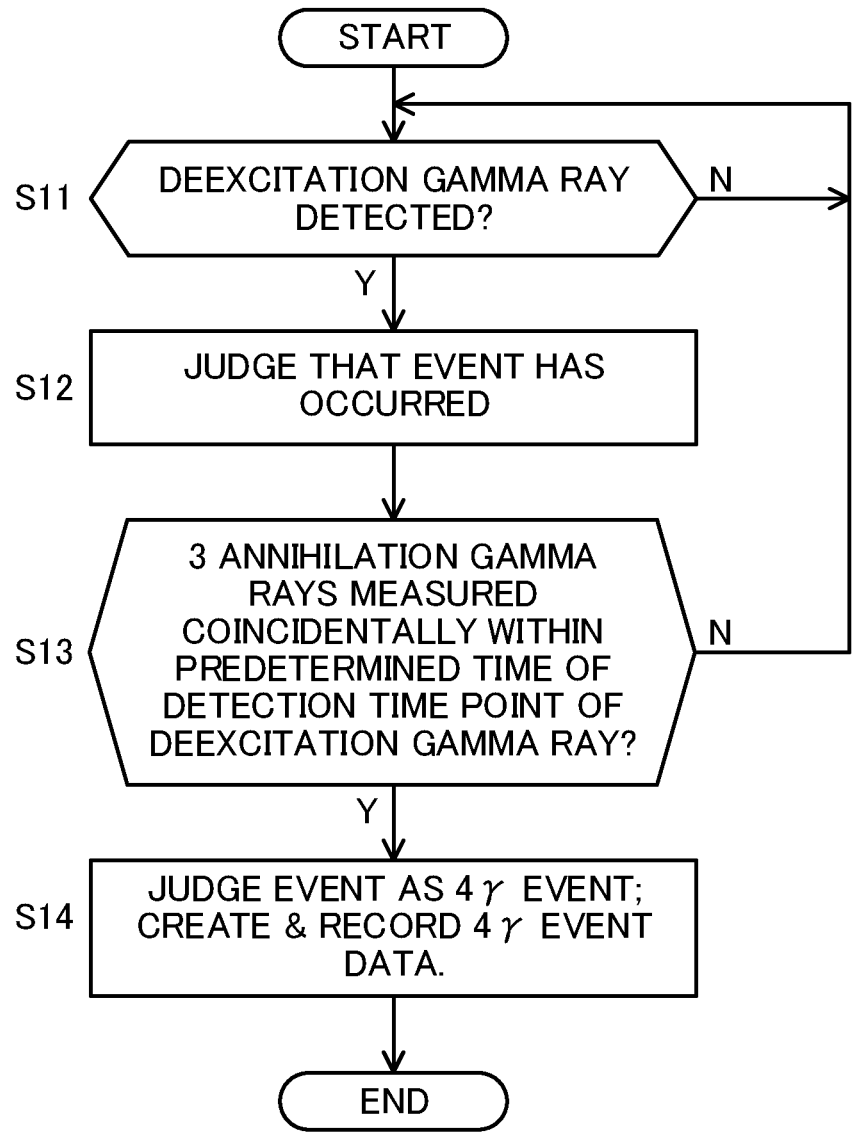
FIG. 9 is a diagram showing an example of a procedure for generating 4γ event data according to an embodiment of the present invention.

FIG. 9 shows, in a simplified manner, one example of the check procedure including the 3γ and 4γ check processes. The check procedure proceeds as follows. At step S11, based on an additional detection signal, whether or not a deexcitation gamma ray has been detected is checked. If, based on the additional detection signal, a deexcitation gamma ray is judged to have been detected ("Y" at step S11), it is judged that one event has occurred (step S12), and the procedure proceeds to step S13. At step S13, based on the additional detection signal and PET detection signals, whether or not three annihilation gamma rays have been measured coincidentally within the predetermined time $T_{WINDOW}$ of the detection time point of the deexcitation gamma ray is checked. If the check result of step S13 is "affirmative", the event is judged to be a 4γ event, so that 4γ event data is created and recorded based on the additional detection signal and the PET detection signals of that event.

The 3γ and 4γ check processes are performed for one event after the next, so that a plurality of sets of 4γ event data are created and recorded. FIG. 10 shows n sets of 4γ event data stored on the data memory 33, where n is an integer of 2 or more. The event number of the 4γ event data created as an i-th set is represented by "i" (where i is a natural number). With respect to the 4γ event data with the event number i, $P_{DET\gamma 1}$ to $P_{DET\gamma 3}$, $t_{DET\gamma 1}$ to $t_{DET\gamma 3}$, $E_{DET\gamma 1}$ to $E_{DET\gamma 3}$, and $t_{DET\gamma E}$, $E_{DET\gamma E}$ are represented by $P_{DET\gamma 1}[i]$ to $P_{DET\gamma 3}[i]$, $t_{DET\gamma 1}[i]$ to $t_{DET\gamma 3}[i]$, $E_{DET\gamma 1}[i]$ to $E_{DET\gamma 3}[i]$, and $t_{DET\gamma E}[i]$, $E_{DET\gamma E}[i]$ respectively.

If the entire energy of a deexcitation gamma ray is absorbed in the deexcitation gamma ray detector 20, the energy $E_{\gamma E}$ of the deexcitation gamma ray is obtained as the detected energy $E_{DET\gamma E}$; in reality, in the deexcitation gamma ray detector 20 occurs not only entire energy absorption but also partial energy absorption such as that due to Compton scattering. When part of the energy of a deexcitation gamma ray is absorbed in the deexcitation gamma ray detector 20, the detected energy $E_{DET\gamma E}$ is lower than the energy $E_{\gamma E}$ of the deexcitation gamma ray. In that case, if the first 4γ check condition described above is adopted, an event that should be recognized as a 4γ event is no longer recognized as such. On the other hand, it does not occur that the energy of each annihilation gamma ray exceeds 511 keV; thus, if an energy exceeding 511 keV is detected, the detected energy is considered to be ascribable to a deexcitation gamma ray. Accordingly, in a case where a positron-emitting nucleus (for example, $^{22}$Na) of which the deexcitation gamma ray has an energy $E_{\gamma E}$ higher than 511 keV is used, it is possible, if the detected energy $E_{DET\gamma E}$ is higher than 511 keV, to judge that the first 4γ check condition is met (that is, it is possible to judge that a gamma ray corresponding to the detected energy $E_{DET\gamma E}$ and detected by the deexcitation gamma ray detector 20 is a deexcitation gamma ray).

—Image Reconstruction—

As shown back in FIG. 8, the signal processor 30 further includes an image reconstructor 34. The image reconstructor 34 generates a distribution image of the target nuclide by performing a process of reconstructing an image based on a plurality of sets of 4γ event data. In the embodiment, the target nuclide is a positron-emitting nucleus in the imaging target TG; accordingly, as a distribution image of the target nuclide, a distribution image of the positron-emitting nucleus is generated. As mentioned previously, a distribution image of a positron-emitting nucleus is a three-dimensional distribution image that shows three-dimensional distribution of the positron-emitting nucleus in XYZ space. In practice, for each 4γ event, based on the detection positions $P_{DET\gamma 1}$ to $P_{DET\gamma 3}$ and the detected energies $E_{DET\gamma 1}$ to $E_{DET\gamma 3}$ of the three annihilation gamma rays included in the 4γ event data, the position of the positron-emitting nucleus that emitted the positron in that 4γ event is determined; the positions determined for different 4γ events are histogrammed into voxels in XYZ space divided in units of a given length. In this way, it is possible to obtain a three-dimensional intensity distribution of the radioactivity ascribable to the positron-emitting nucleus as a distribution image of the positron-emitting nucleus.

Figures 11, 12:
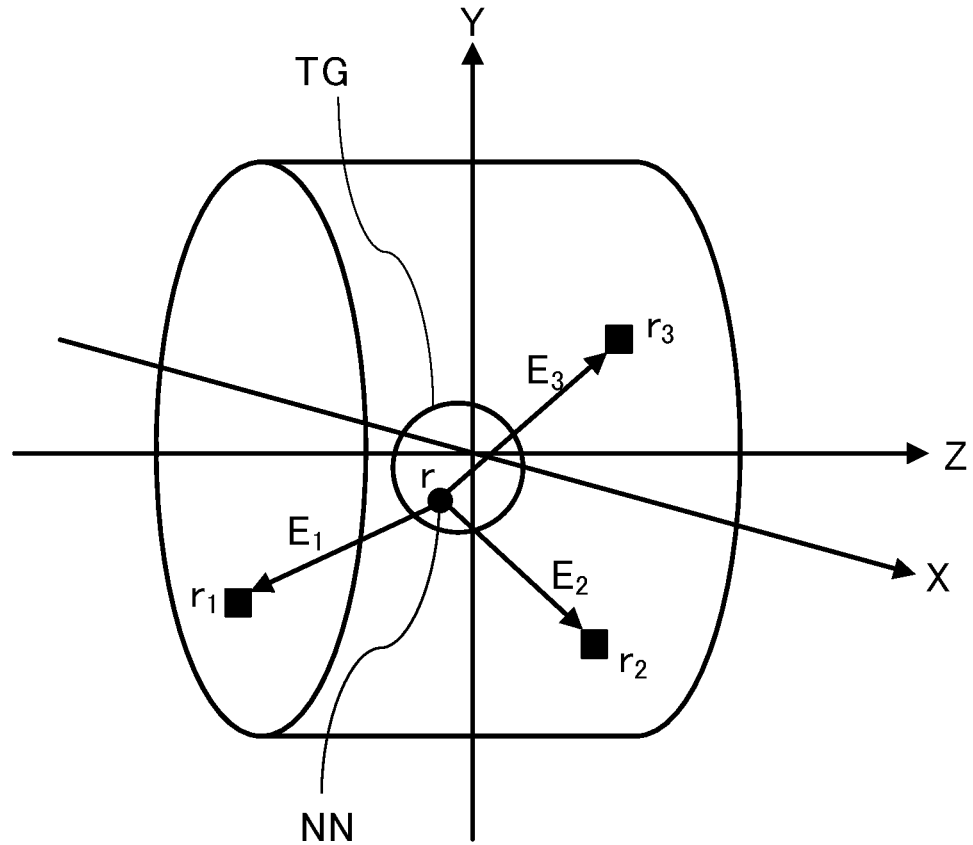
FIG. 11 is a diagram showing a relationship between a positron-emitting nucleus and three annihilation gamma rays.
FIG. 12 shows how a nuclide position and a positron lifetime is determined for each event.

Now, with reference to FIG. 11, a supplemental description will be given of the method of generating a distribution image of a positron-emitting nucleus (for FIG. 11, a diagram is reproduced, partly modified, from Non-Patent Document 7). The cylindrical surface shown in FIG. 11 schematically shows the arrangement face of the plurality of gamma ray detectors 11 constituting the PET detector 10. Suppose, in a given event of interest, a positron is emitted from a positron-emitting nucleus NN present at a position r in the imaging target TG and, when the positron annihilates, three annihilation gamma rays are generated so that the three annihilation gamma rays are detected with position vectors $r_1$, $r_2$, and $r_3$, respectively, in the PET detector 10 (those rays interact with the PET detector 10), the energies of the three annihilation gamma rays being $E_1$, $E_2$, and $E_3$ respectively. Here, the total momentum of the positron and the electron on annihilation equals zero, and thus for the x, y, and z momentum components, the following expressions of momentum conservation hold.

[Expression 1]

$$p_{x1} + p_{x2} + p_{x3} = \frac{E_1}{c} \cdot \frac{x-x_1}{|r-r_1|} + \frac{E_2}{c} \cdot \frac{x-x_2}{|r-r_2|} + \frac{E_3}{c} \cdot \frac{x-x_3}{|r-r_3|} = 0 \quad (1)$$

$$p_{y1} + p_{y2} + p_{y3} = \frac{E_1}{c} \cdot \frac{y-y_1}{|r-r_1|} + \frac{E_2}{c} \cdot \frac{y-y_2}{|r-r_2|} + \frac{E_3}{c} \cdot \frac{y-y_3}{|r-r_3|} = 0 \quad (2)$$

$$p_{z1} + p_{z2} + p_{z3} = \frac{E_1}{c} \cdot \frac{z-z_1}{|r-r_1|} + \frac{E_2}{c} \cdot \frac{z-z_2}{|r-r_2|} + \frac{E_3}{c} \cdot \frac{z-z_3}{|r-r_3|} = 0 \quad (3)$$

$$|r-r_j| = \sqrt{(x-x_j)^2 + (y-y_j)^2 + (z-z_j)^2} \quad (4)$$

In Expressions (1) to (3), c is a constant representing the speed of light. The three annihilation gamma rays comprise a first to a third annihilation gamma ray, and $p_{xi}$, $p_{yi}$, and $p_{zi}$ represent the X-axis, Y-axis, and Z-axis components of the momentum of the i-th annihilation gamma ray. In reality, a positron and an electron on annihilation have a tiny momentum, but it is here assumed to be zero. Then, the vector sum of the momentums of the three annihilation gamma rays equals zero, and the sum of the respective axis components also equals zero.

In Expressions (1) to (3), r represents the position vector of the position where annihilation occurred; x, y, and z represent the X-axis, Y-axis, and Z-axis components, respectively, of the position r; $r_3$ represents the detection position of an annihilation gamma ray with an energy $E_j$; and $x_j$, $y_j$, and $z_j$ represent the X-axis, Y-axis, and Z-axis components, respectively, of the detection position $r_j$ (where j is 1, 2, or 3). Thus, $|r-r_j|$ represents the distance between the position r at which annihilation occurred and the detection position $r_j$ of an annihilation gamma ray. Accordingly, the values found by dividing "$x-x_j$", "$y-y_j$", and "$z-z_j$" by that distance are the X-axis, Y-axis, and Z-axis components of the unit vector with respect to the momentum direction of the three gamma rays.

The distance $|r-r_j|$, as expressed in terms of the annihilation position and the detection position in the X, Y, Z coordinate system, is given by Expression (4) above.

With respect to a 4γ event with an event number i, the image reconstructor 34 solves expressions (1) to (4) taking the detection positions $P_{DET\gamma1}[i]$ to $P_{DET\gamma3}[i]$ and the detected energies $E_{DET\gamma1}[i]$ to $E_{DET\gamma3}[i]$ of the three annihilation gamma rays as positions $r_1$ to $r_3$ and energies $E_1$ to $E_3$, and thereby finds the position r as the position of the positron-emitting nucleus NN that emitted a positron in the 4γ event with the event number i. The position r represents the position of annihilation of the positron; however, in ordinary PET, the range of a positron in the imaging target TG is regarded as small, and the annihilation position r of the positron is determined as the position of the positron-emitting nucleus that emitted the positron; thus, there is a difference corresponding to the range of the positron between the determined probe distribution and the actual probe distribution. Even so, what has to be determined in the present invention is not the distribution of the positron-emitting nucleus but the environment around the position at which annihilation occurred, and therefore using the annihilation position of the positron causes no inconvenience; it is thus possible to obtain, without an error associated with the range, information on the oxygen concentration, the molecular structure, etc. at the position of annihilation.

The determined position of the positron-emitting nucleus is referred to also as the nuclide position, and is represented by the symbol "NP". The nuclide position NP with respect to the event number i will occasionally be represented by NP[i]. By determining the nuclide position NP for each 4γ event, it is possible to obtain nuclide positions NP[1], NP[2], NP[3], . . . NP[n] as shown in FIG. 12.

—Positron Lifetime Derivation—

As shown back in FIG. 8, the signal processor 30 further includes a positron lifetime deriver 35. For each 4γ event, the positron lifetime deriver 35 derives the lifetime of the positron based on the detection time point of the annihilation gamma rays and the detection time point of the deexcitation gamma ray, all included in the 4γ event data. The positron lifetime derived for each 4γ event represents the length of time after a positron is emitted from a positron-emitting nucleus until the positron disappears through annihilation in one event.

The positron lifetime derived for each 4γ event is represented by the symbol "LT". The positron lifetime LT with respect to the event number i, in particular, will occasionally be represented by LT[i]. By determining the positron lifetime LT for each 4γ event, it is possible to obtain positron lifetimes LT[1], LT[2], LT[3], . . . LT[n] as shown in FIG. 12.

With respect to the event number i, the time lag from the detection time point $t_{DET\gamma E}[i]$ of the deexcitation gamma ray to the detection time point of the three annihilation gamma rays is determined as the positron lifetime LT[i]. In the derivation of this time lag, usable as the detection time point of the three annihilation gamma rays is the average time point of the detection time points $t_{DET\gamma1}[i]$ to $t_{DET\gamma3}[i]$ or any one of the detection time points $t_{DET\gamma1}[i]$ to $t_{DET\gamma3}[i]$.

Figure 13:
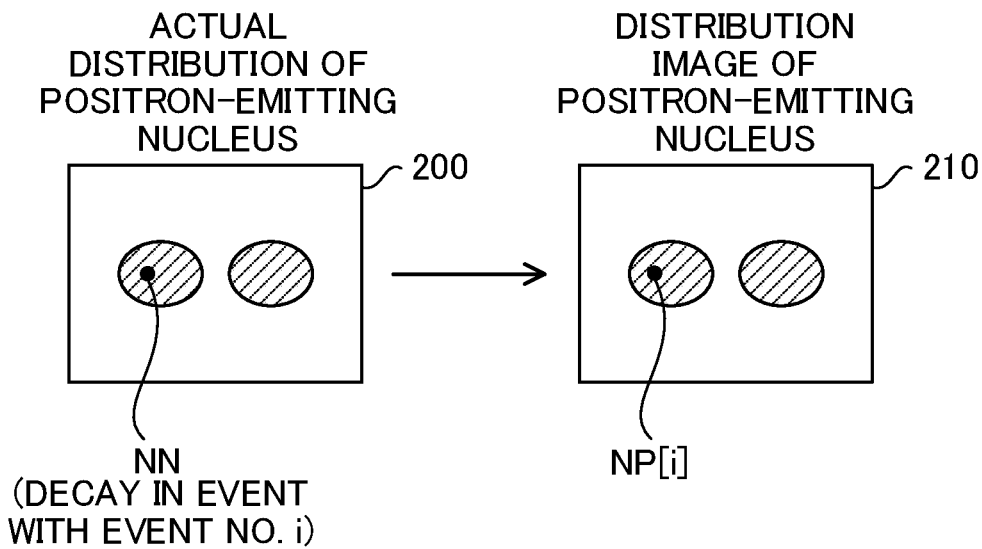
FIG. 13 is a diagram showing actual distribution of a positron-emitting nucleus and a distribution image of the positron-emitting nucleus obtained by image reconstruction.

In FIG. 13, an image 200 with hatched regions shows the actual distribution of a positron-emitting nucleus in the imaging target TG, and an image 210 is a distribution image of that positron-emitting nucleus as generated by the image reconstructor 34. Histograming the nuclide positions NP[1] to NP[n] determined with respect to the event numbers 1 to n into voxels in XYZ space results in generating a distribution image 210 of the positron-emitting nucleus in the imaging target TG. Although, in FIG. 13, the images 200 and 210 are illustrated as two-dimensional images, in reality they are three-dimensional images (the same is true with any of the diagrams referred to later which show an actual distribution of a positron-emitting nucleus or a distribution image of a positron-emitting nucleus in the imaging target TG).

On occurrence of a 4γ event with an event number i based on radioactive decay of a given positron-emitting nucleus NN in the imaging target TG, then at the position NP[i] in the image 210 corresponding to the position at which positron annihilation occurred, a voxel value indicating the presence of a positron-emitting nucleus NN is added; on the other hand, the lifetime of the positron from the positron-emitting nucleus NN that was present at the position NP[i] is determined as LT[i]. The same applies to any 4γ event ascribable to a positron-emitting nucleus other than the positron-emitting nucleus NN.

As described above, based on a PET detection signal and an additional detection signal, the signal processor 30 generates a plurality of sets of 4γ event data with respect to a plurality of 4γ events; then based on the plurality of sets of 4γ event data, the signal processor 30 can derive the state of distribution of a positron-emitting nucleus in the imaging target TG in three dimensions and determine the positron lifetime in association with each distribution position thus derived.

More specifically, for each 4γ event in which three annihilation gamma rays are measured coincidentally within a predetermined time $T_{WINDOW}$ of the detection time point ($t_{DET\gamma E}$) of a deexcitation gamma ray, the signal processor 30 derives the positron annihilation position in that 4γ event as the position (NP) of the positron-emitting nucleus that emitted a positron in that 4γ event, and also determines the time lag from the detection time point ($t_{DET\gamma E}$) of a deexcitation gamma ray to the detection time point (such as the average of $t_{DET\gamma1}$ to $t_{DET\gamma3}$) at which three annihilation gamma rays are measured coincidentally as the positron lifetime (LT) in that 4γ event, based on the detected energies ($E_{DET\gamma1}$ to $E_{DET\gamma3}$) and the detection positions ($P_{DET\gamma1}$ to $P_{DET\gamma3}$) of the three annihilation gamma rays as detected by the PET detector 10.

Then, based on the positions (NP[1] to NP[n]) of the positron-emitting nucleus estimated, and the positron lifetimes (LT[1] to LT[n]) derived, with respect to a plurality of 4γ events, the signal processor 30 can generate a three-dimensional distribution image of the positron-emitting nucleus and derive information on the positron lifetime individually at each position in the three-dimensional distribution image. Information on the positron lifetime is an index of the lifetime of the positron, and is, for example, the half-life of the positron. An example of derivation of the half-life of a positron will be described later.

For the sake of convenience, the configuration, operation, and other features of the PET system 1 described above will be referred to as the basic practical example. The following description deals with, as a plurality of practical examples, application examples, modified examples, and the like of the PET system 1. Unless expressly stated, or unless inconsistent, any description of the basic practical example applies to the practical examples described below; for any description of a practical example that is inconsistent with the basic practical example, that description of the practical example prevails. Unless inconsistent, any feature of any of the plurality of practical examples described below can be applied to any other of the practical examples (that is, any two or more of the plurality of practical examples can be combined together).

First Practical Example

Figure 14:
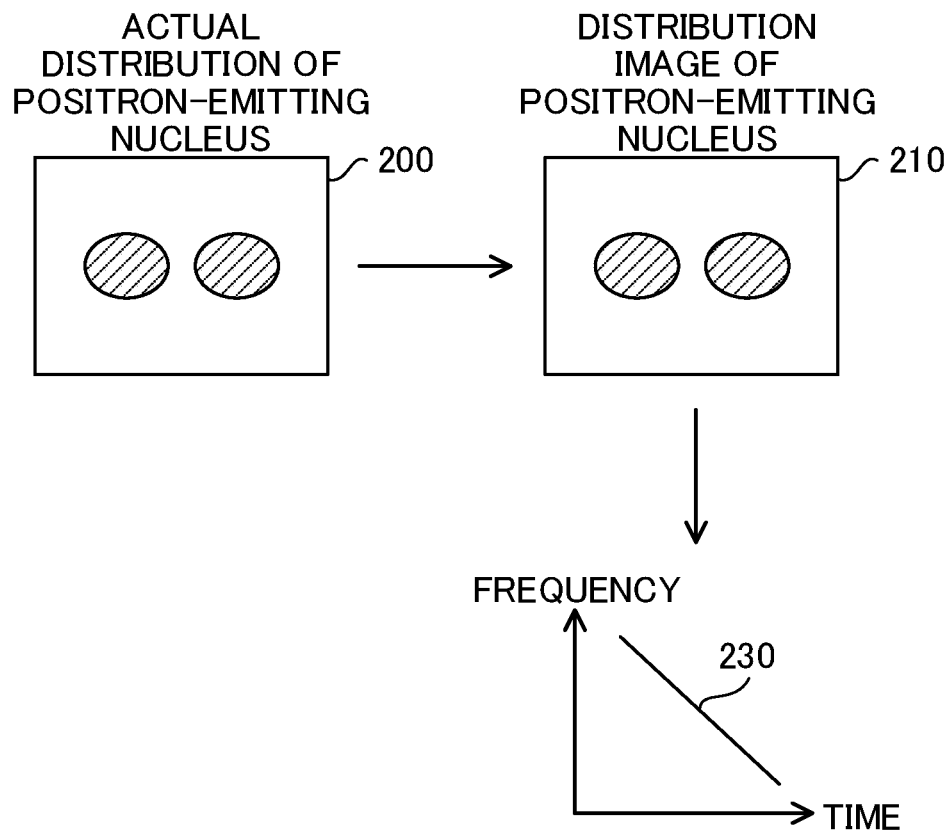
FIG. 14 is a diagram showing actual distribution of a positron-emitting nucleus and a distribution image of the positron-emitting nucleus obtained by image reconstruction along with a positron lifetime spectrum.

A first practical example will be described. In FIG. 14, a line 230 represents a positron lifetime spectrum obtained by histograming the positron lifetimes LT[1] to LT[n] determined with respect to the event numbers 1 to n. The positron lifetime spectrum 230 is a histogram which plots the positron lifetimes LT[1] to LT[n] determined with respect to the event numbers 1 to n with time taken along the horizontal axis and frequency taken along the vertical axis.

The positron lifetime deriver 35 generates a positron lifetime spectrum 230, and can also, based on the gradient of the positron lifetime spectrum 230, determine the average half-life of the positron in a region in the imaging target TG where a positron-emitting nucleus is present. In a positron lifetime spectrum (histogram) like the positron lifetime spectrum 230, the gradient of the positron lifetime spectrum depends on the half-life of the positron. The steeper the gradient, the shorter the half-life of the positron. The method of determining the half-life of a positron based on the gradient of a positron lifetime spectrum is itself well-known in positron annihilation lifetime spectroscopy (PALS) (see Non-Patent Documents 2 and 3 identified earlier).

An actual positron lifetime spectrum describes an exponential curve; on a single logarithmic chart, one involving a single half-life component describes a straight line and one involving a plurality of half-life components describes a curve. For the sake of simplicity, in FIG. 14, a positron lifetime spectrum is represented by a line segment. The same is true with any of the diagrams referred to later which shows a positron lifetime spectrum. Conversely, it is also possible, instead of creating a positron lifetime spectrum for each position, to create a positron lifetime spectrum with respect to all events and then divide the positron lifetime spectrum into time segments to obtain, in each of those time segments, a distribution image of the position where annihilation occurred.

Second Practical Example

Figure 15:
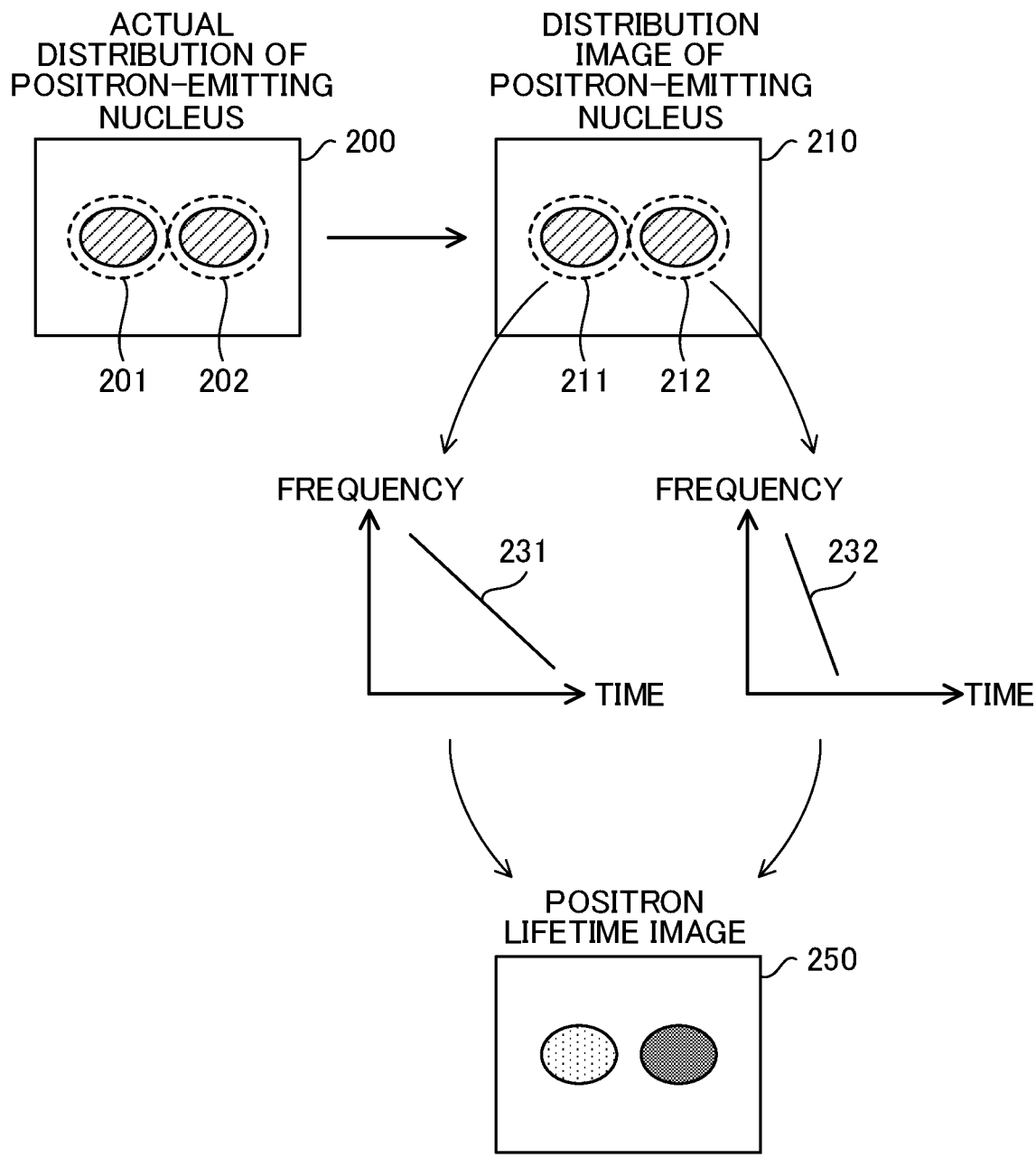
FIG. 15 is a diagram showing actual distribution of a positron-emitting nucleus, a distribution image of the positron-emitting nucleus obtained by image reconstruction, and positron lifetime spectra derived for different regions respectively, along with a positron lifetime image.

A second practical example will be described. FIG. 15 will be referred to. For the sake of concrete description, it is here assumed that the positron-emitting nucleus is distributed in each of regions 201 and 202 in the imaging target TG that are located away from each other. Then, in a distribution image 210 of the positron-emitting nucleus, a distribution image corresponding to the region 201 appears in a region 211 and a distribution image corresponding to the region 202 appears in a region 212.

The positron lifetime deriver 35 can determine the positron lifetime spectrum and the half-life of the positron in any region in the imaging target TG (on the assumption, however, that a plurality of 4γ events have occurred based on radioactive decay of the positron-emitting nucleus in that region). From the 4γ event data based on radioactive decay of the positron-emitting nucleus in the region 201, the positron lifetime spectrum 231 and the half-life of the positron with respect to the region 201 or 211 can be determined; from the 4γ event data based on radioactive decay of the positron-emitting nucleus in the region 202, the positron lifetime spectrum 232 and the half-life of the positron with respect to the region 202 or 212 can be determined.

For the sake of concrete description, assume that the 4γ events with the event numbers 1 to n/2 are events based on radioactive decay of the positron-emitting nucleus in the region 201, and that the 4γ events with the event numbers (n/2+1) to n are events based on radioactive decay of the positron-emitting nucleus in the region 202. Then, a positron lifetime spectrum 231 is a time spectrum obtained by histograming the positron lifetimes LT[1] to LT[n/2] determined with respect to the event numbers 1 to n/2 (a histogram of the positron lifetimes LT[1] to LT[n/2] with time taken along the horizontal axis and frequency taken along the vertical axis); a positron lifetime spectrum 232 is a time spectrum obtained by histograming the positron lifetimes LT[n/2+1] to LT[n] determined with respect to the event numbers (n/2+1) to n (a histogram of the positron lifetimes LT[n/2+1] to LT[n] with time taken along the horizontal axis and frequency taken along the vertical axis).

Based on the gradient of the positron lifetime spectrum 231, the half-life of the positron in the region 201 can be determined, and based on the gradient of the positron lifetime spectrum 232, the half-life of the positron in the region 202 can be determined. That is, it is possible to derive, individually, information on the positron lifetime at the position of the region 211 and information on the positron lifetime at the position of the region 212 in the distribution image 210. Information on the positron lifetime is an index of the lifetime of the positron, and is here the half-life of the positron.

It is here assumed that the numbers of voxels that belong to the regions 211 and 212 respectively are each one or more. Accordingly, for example, if the region 211 comprises a first to a hundredth voxel, the region 201 in the imaging target TG in real space comprises a first to a hundredth voxel in the distributed image 210. However, the number of voxels that belong to the region 211 may be one. The same applies to the region 212.

Although the above description deals with an example where information on the positron lifetime (here, the half-life) is derived individually in each of wo regions, it is also possible to derive information on the positron lifetime (here, the half-life) individually in each of three or more regions. Conversely, it is also possible, instead of creating a positron lifetime spectrum for each position, to create a positron lifetime spectrum with respect to all events and then divide the positron lifetime spectrum into time segments to obtain, in each of those time segments, a distribution image of the position where annihilation occurred.

In the signal processor 30, obtaining information on the positron lifetime (here, the half-life) at each position in the image 210 and replacing the voxel value at each position in the image 210 with the information on the positron lifetime at the corresponding position results in obtaining a positron lifetime image (three-dimensional positron lifetime image) 250 which shows the information on the positron lifetime rendered into a three-dimensional image (see FIG. 15). The positron lifetime image 250 is an image that shows, in three dimensions, distribution of the positron-emitting nucleus in the imaging target TG and information on the positron lifetime at each distribution position of the positron-emitting nucleus in the imaging target TG (more precisely, information on the positron lifetime at each position in a region in the imaging target TG where the positron-emitting nucleus is present).

In the present invention, information on the positron lifetime may be any index other than the half-life so long as it is an index of the lifetime of the positron. For example, in the specific example described above, the average lifetime (as expressed in terms of natural logarithm) of the positron lifetimes LT[1] to LT[n/2] may be calculated as information on the positron lifetime in the regions 201 and 211 and in the regions region 202 and 212.

Third Practical Example

A third practical example will be described. Some studies have found the following: the lifetime of the positron in liquid depends on oxygen concentration in the liquid, the lifetime of the positron decreasing as the oxygen concentration increases (see Non-Patent Document 4 identified earlier). Based on the findings, application examples as described below are conceivable.

A drug that concentrates in blood in a living body (that circulates with blood) is labeled with a type B positron-emitting nucleus to prepare a positron-emitting nucleus probe. A living body administered with the positron-emitting nucleus probe is taken as the imaging target TG. Then, it is possible to obtain, from a group of 4γ event data, information on the positron lifetime at each position in the living body, and to estimate, from the information on the positron lifetime at each position in the living body, the blood oxygen level at each position in the living body. That is, it is possible to render the blood oxygen level in a living body into a three-dimensional image in a non-invasive manner. While techniques for measuring the blood oxygen level near the body surface by exploiting absorption of infrared light are known, no technique is conventionally known that visualizes the blood oxygen level in a deep part in a living body in a non-invasive and direct manner, and developing such a technique will prove extremely useful.

For example, the blood oxygen level in the brain of a living body as the imaging target TG can be rendered into a three-dimensional image. This makes it possible to conduct detailed diagnosis of brain functions in a non-invasive manner. More specifically, for example, grasping that the blood oxygen level in a first part in the brain is normal but that the blood oxygen level in a second part in the brain is abnormally low helps identify a possibility of a lesion in the second part of the brain.

For another example, the blood oxygen level in the heart of a living body as the imaging target TG can be rendered into a three-dimensional image. This makes it possible to conduct detailed diagnosis of the heart (to diagnose for the presence of a heart disease) in a non-invasive manner. Currently, catheterization of the heart is performed to measure the blood oxygen level in the heart, and it involves inserting a catheter into the blood vessel. With the PET system 1, it is possible to diagnose for the presence of a heart disease with far less burden on the living body than by catheterization.

For another example, it is conceivable to use the PET system 1 to diagnose for infection with anaerobic bacteria. It is believed that, as the number of anaerobic bacteria present in a part of a living body increases, the blood oxygen level in that part decreases. Thus, rendering the blood oxygen level in a living body into a three-dimensional image is expected to provide useful information in diagnosis for and treatment of infection with anaerobic bacteria.

Fourth Practical Example

A fourth practical example will be described. With PALS, it is possible to analyze the structure of a substance through measurement of the lifetime of the positron. For example, it is known that the lifetime of the positron varies greatly with, for example, the presence of holes in a solid, and therefore PALS is used in analysis of semiconductor materials in the fields of material engineering (see Non-Patent Documents 2 and 3). Applying this technique using the PET system 1 makes it possible to obtain information reflecting a structure in a living body in a non-invasive manner. For example, application examples as described below are conceivable.

A drug that concentrates in cancerous cells in a living body is labeled with a type B positron-emitting nucleus to prepare a positron-emitting nucleus probe. A living body administered with the positron-emitting nucleus probe is taken as the imaging target TG. Then, it is possible to obtain, from a group of 4γ event data, information on the positron lifetime in the cancerous cells in the living body, and to estimate, from the information on the lifetime, the physical structure of the cancerous cells, thereby to diagnose the stage of lesion advancement or otherwise obtain pathological information. The positron lifetime is considered to vary, not only with oxygen concentration (oxygen level) as mentioned above, but also with other various parameters including concentrations of gases other than oxygen, ion concentrations like hydrogen ion concentration, and temperature. Thus, various applications of the present invention are conceivable that involve measurement of those parameters.

Fifth Practical Example

A fifth practical example will be described. In the basic practical example described previously, in addition to a PET detector 10 as provided in existing PET systems, a deexcitation gamma ray detector 20 for detecting deexcitation gamma rays is provided separately (see FIG. 6). Instead, the PET detector 10 may be configured to function also as a deexcitation gamma ray detector 20. Specifically, at least part of the group of gamma ray detectors 11 constituting the PET detector 10 may be configured to function as the deexcitation gamma ray detector 20 (in other words, the deexcitation gamma ray detector 20 may be configured to employ at least part of the group of gamma ray detectors 11) so that the PET detector 10 carries out both the operation of the PET detector 10 and the operation of the deexcitation gamma ray detector 20. In this way, it is possible to apply the present invention to existing PET systems.

Sixth Practical Example

A sixth practical example will be described. Examples of type B positron-emitting nuclei that can be used in the PET system 1 and that can be contained in the imaging target TG include $^{14}$O, $^{22}$Na, $^{34m}$Cl, $^{38}$K, $^{44}$Sc, $^{48}$V, $^{52}$Mn, $^{52m}$Mn, $^{52}$Fe, $^{60}$Cu, $^{72}$As, $^{76}$Br, $^{82m}$Rb, $^{94m}$Tc, $^{104m}$Ag, $^{110}$In, and $^{124}$I. These are just typical nuclides that emit deexcitation gamma rays at rates as high as around 90%, and other nuclides with lower rates of emission can also be used.

In a type B positron-emitting nucleus, there is a time lag after emission of a positron until emission of a deexcitation gamma ray. However, unless the excited state of the daughter nucleus has an especially long half-life, the time lag is of the order of femtoseconds to picoseconds, which is shorter than the time resolution of common radiation detectors.

In the PET system 1, the detection time point of a deexcitation gamma ray is taken as the emission time point of a positron, and the lifetime of the positron is found as the lifetime of orthopositronium. Accordingly, as compared with this lifetime, the half-life of the daughter nucleus from the excited state to the ground state should be sufficiently short. The half-life of orthopositronium in a substance is about several nanoseconds to several tens of nanoseconds, and thus a positron-emitting nucleus in which the half-life of the daughter nucleus from the excited state to the ground state is of the order of femtoseconds to picoseconds can be used in the PET system 1 with no problem. Some nuclides (called nuclear isomers) that undergo type B radioactive decay have extremely long lifetimes of the excited state, and these nuclides are unsuitable for the PET system 1.

In a positron-emitting nucleus, beta decay does not always lead to emission of a positron; positron emission competes with electron capture (the phenomenon in which a proton captures an electron orbiting around the atomic nucleus and turns into a neutron). That is, the two processes, positron emission and electron capture, compete with each other, with the result that only one of them takes place. The probabilities with which positron emission and electron capture respectively occur depend on the nuclide. It is preferable to use a nuclide with as high a probability of positron emission as possible in the PET system 1.

Seventh Practical Example

A seventh practical example will be described. The signal processor 30 can be configured to perform processing as described below.

When PET detection signals indicating that three gamma rays have been detected in the PET detector 10 are fed in, in the 3γ check process in the basic practical example described previously, it is checked whether the three annihilation gamma rays have been measured coincidentally. In contrast, in the 3γ check process in the seventh practical example, it is checked whether or not three gamma rays that can be three annihilation gamma rays have been measured coincidentally. That is, in the seventh practical example, when PET detection signals indicating that three gamma rays have been detected in the PET detector 10 are fed in, a 3γ check process in which the PET detection signals indicate coincidental measurement of three gamma rays is checked is performed.

Specifically (see FIG. 8), when three PET detection signals $SG_{\gamma 1}$, $SG_{\gamma 2}$, and $SG_{\gamma 3}$ indicating that a total of three gamma rays have been detected at three mutually different positions, respectively, in the PET detector 10 are fed to the signal processor 30, the 3γ coincident measurement checker 31 identifies, based on the input time points of the PET detection signals $SG_{\gamma 1}$, $SG_{\gamma 2}$, and $SG_{\gamma 3}$, the detection time points $t_{DET\gamma 1}$, $t_{DET\gamma 2}$, and $t_{DET\gamma 3}$ of the three gamma rays and identifies, based on the energy information included in the PET detection signals $SG_{\gamma 1}$, $SG_{\gamma 2}$, and $SG_{\gamma 3}$, the detected energies $E_{DET\gamma 1}$, $E_{DET\gamma 2}$, and $E_{DET\gamma 3}$ of the three gamma rays.

If the three coincidentally measured gamma rays are annihilation gamma rays, the energy of each gamma ray does not exceed 511 keV. Accordingly, if the detection time points $t_{DET\gamma 1}$ to $t_{DET\gamma 3}$ coincide and in addition the detected energies $E_{DET\gamma 1}$ to $E_{DET\gamma 3}$ are each equal to or less than 511 keV, then in the 3γ check process, the 3γ coincident measurement checker 31 judges that three gamma rays that can be three annihilation gamma rays have been measured coincidentally; otherwise, the 3γ coincident measurement checker 31 does not judge so. As mentioned previously, the concept of coincidence here allows for a predetermined width of time.

The PET detector 10 or the signal processor 30 may be configured such that only such PET detection signals as include energy information indicating that the detected energy is equal to or less than 511 keV are fed to the 3γ coincident measurement checker 31. In that case, when three PET detection signals $SG_{\gamma 1}$, $SG_{\gamma 2}$, and $SG_{\gamma 3}$ are fed to the 3γ coincident measurement checker 31, the 3γ coincident measurement checker 31 simply checks whether or not the detection time points $t_{DET\gamma 1}$ to $t_{DET\gamma 3}$ coincide so that, regardless of the detected energies $E_{DET\gamma 1}$ to $E_{DET\gamma 3}$, if the detection time points $t_{DET\gamma 1}$ to $t_{DET\gamma 3}$ coincide, the 3γ coincident measurement checker 31 judges that three gamma rays that can be three annihilation gamma rays have been measured coincidentally.

On judging, based on the PET detection signals $SG_{\gamma 1}$ to $SG_{\gamma 3}$ fed in, that three gamma rays that can be annihilation gamma rays have been measured coincidentally, the 3γ coincident measurement checker 31 takes the three gamma rays as three candidate gamma rays and, referring to the PET detection signals $SG_{\gamma 1}$ to $SG_{\gamma 3}$, records 3γ event data including the detection positions $P_{DET\gamma 1}$ to $P_{DET\gamma 3}$, the detected energies $E_{DET\gamma 1}$ to $E_{DET\gamma 3}$, and the detection time points $t_{DET\gamma 1}$ to $t_{DET\gamma 3}$ of the three candidate gamma rays to the data memory 33.

On the other hand, the signal processor 30 can be provided with a deexcitation gamma ray checker (not illustrated). When fed with an additional detection signal $SG\gamma_E$ indicating that a gamma ray has been detected in the deexcitation gamma ray detector 20, the deexcitation gamma ray checker identifies, based on the input time point of the additional detection signal $SG\gamma_E$, the detection time point $t_{DET\gamma E}$ of that gamma ray and identifies, based on the energy information included in the additional detection signal $SG\gamma_E$, the detected energy $E_{DET\gamma E}$ of that gamma ray. The deexcitation gamma ray detector then simply checks whether or not the detected energy $E_{DET\gamma E}$ meets the first 4γ check condition described previously so that, if the detected energy $E_{DET\gamma E}$ meets the first 4γ check condition, the deexcitation gamma ray detector judges that an annihilation gamma ray has been detected and records, while referring to the additional detection signal $SG\gamma_E$, 1γ event data including the detected energy $E_{DET\gamma E}$ and the detection time point $t_{DET\gamma E}$ of the annihilation gamma ray to the data memory 33. The detected energy $E_{DET\gamma E}$, which has already been used in judgement, does not necessarily have to be included in the 1γ event data.

By recording, with a common time stamp, the data based on the PET detection signals $SG_{\gamma 1}$ to $SG_{\gamma 3}$ and the additional detection signal $t_{DET\gamma E}$, it is possible to record the 3γ event data originating from the PET detector 10 and the 1γ event data originating from the deexcitation gamma ray detector 20 including the recording of the detection time points $t_{DET\gamma1}$ to $t_{DET\gamma3}$ and $t_{DET\gamma E}$. By performing such recording repeatedly throughout an imaging period, a plurality of sets of event data are recorded to the data memory 33.

Afterwards, in off-line analysis, the signal processor 30 extracts, from the data recorded on the data memory 33, 4γ event data constituting 4γ events and records it to the data memory 33.

For example, consider given 3γ event data and given 1γ event data recorded on the data memory 33, identified as 3γ event data $DT_3$ and 1γ event data $DT_1$ respectively. With these data, the signal processor 30 checks whether or not the first and second conditions described below are met.

The first condition is that the sum of the detected energies $E_{DET\gamma1}$ to $E_{DET\gamma3}$ included in the 3γ event data $DT_3$ equals 1022 keV. As mentioned previously, the concept of equality here allows for a predetermined width determined with consideration given to the energy resolution of the PET detector 10. If the first condition is met, the three gamma rays corresponding to the 3γ event data $DT_3$ are judged to be three annihilation gamma rays. If the first condition is not met, it is no longer necessary to check whether or not the second condition is met. Thus, the following description discussing the second condition assumes that the three gamma rays corresponding to the 3γ event data $DT_3$ are three annihilation gamma rays.

The second condition is that, with the average time point of the detection time points $t_{DET\gamma1}$ to $t_{DET\gamma3}$ included in the 3γ event data $DT_3$ or any one of the detection time points $t_{DET\gamma1}$ to $t_{DET\gamma3}$ taken as the detection time point of three annihilation gamma rays and with the detection time point $t_{DET\gamma E}$ included in the 1γ event data $DT_1$ taken as the detection time point of a deexcitation gamma ray, the time lag between the detection time point of the deexcitation gamma ray and the detection time point of the annihilation gamma rays is within a predetermined time $T_{WINDOW}$.

Only if the first and second conditions are both met with respect to the 3γ event data $DT_3$ and the 1γ event data $DT_1$, the signal processor 30 (for example, the 4γ event checker 32) judges that the three gamma rays corresponding to the 3γ event data $DT_3$ and the one gamma ray corresponding to the 1γ event data $DT_1$ constitute a 4γ event, and records the combination of the 3γ event data $DT_3$ and the 1γ event data $DT_1$ as 4γ event data to the data memory 33.

Such operation is repeated for all combinations of 3γ event data and 1γ event data recorded on the data memory 33, so that a plurality of sets of 4γ event data are recorded to the data memory 33. Any set of 3γ event data, once used to create a set of 4γ event data, is never used again to create another set of 4γ event data. The same applies to 1γ event data. The operation after the recording of 4γ event data is as described previously.

A configuration is also possible where, every time a PET detection signal including energy information indicating that the detected energy is equal to or less than 511 keV is fed to the signal processor 30, the position information and the energy information included in the PET detection signal is, with the above-mentioned time stamp added to it, recorded to the data memory 33 and, every time an additional detection signal that meets the first 4γ check condition is fed to the signal processor 30, the energy information included in the additional detection signal is, with the above-mentioned time stamp added to it, recorded to the data memory 33. Such recording is performed repeatedly throughout a predetermined imaging period. Afterwards, with desired timing, the signal processor 30 extracts, from what is recorded on the data memory 33, data constituting 4γ events and, based on the 4γ event data reflecting the extracted data, performs various kinds of processing including generation of a distribution image of the positron-emitting nucleus and derivation of information on the positron lifetime.

In any case, so long as 4γ event data as described in connection with the basic practical example is obtained eventually, the check of whether a detected gamma ray is an annihilation gamma ray or not, the check for coincident measurement, etc. may be performed at any stage.

Eighth Practical Example

An eighth practical example will be described. Two or more type B nuclides (type B positron-emitting nuclei) of which deexcitation gamma rays have mutually different energies can be contained in the imaging target TG. In that case, by referring to the energy information included in an additional detection signal, it is possible to identify from which of the two or more type B nuclides a gamma ray detected by the deexcitation gamma ray detector 20 was emitted. Based on the results of such identification, it is possible to obtain a three-dimensional distribution image, information on the positron lifetime, etc. for each type B nuclide.

Ninth Practical Example

A ninth practical example will be described. The different kinds of processing performed in the signal processor 30 is implemented basically as a combination of hardware and software. Some of the functions performed by the signal processor 30 can be implemented as hardware or software. In a case where a particular function is implemented as software, the particular function can be coded as a program so that running the program on a program execution device (for example, a microcomputer constituting the signal processor 30) permits the function to be performed. Such a program can be stored and fixed in any recording medium. A recording medium in which the program is stored and fixed can be incorporated in, or connected to, a device (such as a server) separate from the signal processor 30

<<Studies on the Present Invention>>

To follow are studies on the present invention.

A PET system $W_1$ (see, for example, FIGS. 6, 8, 10, and 12 in particular) according to one aspect of the present invention is a PET system with a positron lifetime measurement function, and includes: a first gamma ray detector (10) configured to receive, from an imaging target (TG) containing a nuclide that goes into an excited state of a daughter nucleus by undergoing beta decay and that then, subsequently to emission of a positron resulting from the beta decay, emits a deexcitation gamma ray when transiting into a ground state of the daughter nucleus, three annihilation gamma rays resulting from the positron annihilating with an electron, thereby to detect the three annihilation gamma rays; a second gamma ray detector (20) configured to detect the deexcitation gamma ray; and a processor (30) configured to derive, in three dimensions, a distribution state of the nuclide in the imaging target, and to determine information on a positron lifetime in association with a derived distribution position, based on the detected energy ($E_{DET\gamma1}$ to $E_{DET\gamma3}$) and the detection position ($P_{DET\gamma1}$ to $P_{DET\gamma3}$) of each of the annihilation gamma rays as detected by the first gamma ray detector as well as the detection time point ($t_{DET\gamma1}$ to $t_{DET\gamma3}$) of the annihilation gamma rays as detected by the first gamma ray detector and the detection time point ($t_{DET\gamma E}$) of the deexcitation gamma ray as detected by the second gamma ray detector.

It is thus possible to know the distribution state of the nuclide and also obtain information on the positron lifetime at each distribution position of the nuclide. This is expected to make it possible to grasp properties (oxygen concentration, molecular structure, etc.) at each position in the imaging target in a non-invasive manner. This is considered to bring about new analysis methods (contributing to diagnosis of brain functions and heart diseases) in the field of life science and the like.

Specifically, for example, in the PET system $W_1$, preferably, the processor is configured to generate a three-dimensional distribution image (for example, the distribution image 210) of the nuclide in the imaging target, and to derive the information (for example, the half-life) on the positron lifetime individually at each of a plurality of positions in the three-dimensional distribution image, based on the detected energy and the detection position of each of the annihilation gamma rays as well as the detection time point of the annihilation gamma rays and the detection time point of the deexcitation gamma ray.

More specifically, for example, in the PET system $W_1$, preferably, the processor is configured, for each event (4γ event) in which the three annihilation gamma rays have been measured coincidentally within a predetermined time of the detection time point of the deexcitation gamma ray, to estimate the positron annihilation position (NP[i] in the example in FIG. 12) in the event, and to derive, as the positron lifetime (LT[i] in the example in FIG. 12) in the event, the time difference from the detection time point of the deexcitation gamma ray to the detection time point at which the three annihilation gamma rays have been measured coincidentally, based on the detected energy and the detection position of each of the annihilation gamma rays. Preferably, the processor is configured further to generate the three-dimensional distribution image, and to derive the information on the positron lifetime individually at a plurality of positions in the three-dimensional distribution image, based on the positron annihilation position (NP[1] to NP[n] in the example in FIG. 12) estimated and the positron lifetime (LT[1] to LT[n] in the example in FIG. 12) derived for a plurality of events.

Instead, in the PET system $W_1$, preferably, the processor is configured to generate a positron lifetime image (for example, the positron lifetime image 250) that shows, in three dimensions, distribution of the nuclide in the imaging target and information on the positron lifetime at each distribution position of the nuclide in the imaging target based on the detected energy and the detection position of each of the annihilation gamma rays as well as the detection time point of the annihilation gamma rays and the detection time point of the deexcitation gamma ray.

More specifically, for example, in the PET system $W_1$, preferably, the processor is configured, for each event (4γ event) in which the three annihilation gamma rays have been measured coincidentally within a predetermined time of the detection time point of the deexcitation gamma ray, to estimate the positron annihilation position (NP[i] in the example in FIG. 12) in the event, and to derive, as the positron lifetime (LT[i] in the example in FIG. 12) in the event, the time difference from the detection time point of the deexcitation gamma ray to the detection time point at which the three annihilation gamma rays have been measured coincidentally, based on the detected energy and the detection position of each of the annihilation gamma rays. Preferably, the processor is configured further to generate the positron lifetime image based on the positron annihilation position (NP[1] to NP[n] in the example in FIG. 12) estimated and the positron lifetime (LT[1] to LT[n] in the example in FIG. 12) derived for a plurality of events.

For another example, in the PET system $W_1$, preferably, the second gamma ray detector comprises a gamma ray detector provided separately from the first gamma ray detector.

Instead, in the PET system $W_1$, preferably, the second gamma ray detector comprises at least part of a group of gamma ray detectors constituting the first gamma ray detector.

A method $W_2$ according to another aspect of the present invention of measuring the lifetime of a positron in a PET system is a method for use in a PET system (1) including a first gamma ray detector (10) configured to receive, from an imaging target (TG) containing a nuclide that goes into an excited state of a daughter nucleus by undergoing beta decay and that then, subsequently to emission of a positron resulting from the beta decay, emits a deexcitation gamma ray when transiting into a ground state of the daughter nucleus, three annihilation gamma rays resulting from the positron annihilating with an electron, thereby to detect the three annihilation gamma rays, and a second gamma ray detector (20) configured to detect the deexcitation gamma ray, and includes deriving, in three dimensions, a distribution state of the nuclide in the imaging target and determining information on a positron lifetime in association with a derived distribution position, based on the detected energy ($E_{DET\gamma1}$ to $E_{DET\gamma3}$) and the detection position ($P_{DET\gamma1}$ to $P_{DET\gamma3}$) of each of the annihilation gamma rays as detected by the first gamma ray detector as well as the detection time point ($t_{DET\gamma1}$ to $t_{DET\gamma3}$) of the annihilation gamma rays as detected by the first gamma ray detector and the detection time point ($t_{DET\gamma E}$) of the deexcitation gamma ray as detected by the second gamma ray detector.

The embodiments of the present invention allow for many modifications made as necessary within the scope of the technical concept set forth in the appended claims. The embodiments described above are merely examples of how the present invention can be implemented, and the senses of the terms used to define the present invention and its features are not limited to those in which they are used in the description of the embodiments given above. All specific values mentioned in the above description are merely examples, and can naturally be altered to different values.

REFERENCE SIGNS LIST

1 PET system
10 PET detector
11 gamma ray detector
20 deexcitation gamma ray detector
21 gamma ray detector
30 signal processor

The invention claimed is:

1. A PET system with a positron lifetime measurement function, comprising:
   a first gamma ray detector configured to receive, from an imaging target containing a nuclide that goes into an excited state of a daughter nucleus by undergoing beta decay and that then, subsequently to emission of a positron resulting from the beta decay, emits a deexcitation gamma ray when transiting into a ground state of the daughter nucleus, three annihilation gamma rays resulting from the positron annihilating with an electron, the first gamma ray detector thereby detecting the three annihilation gamma rays;

a second gamma ray detector provided separately from the first gamma ray detector and configured to detect the deexcitation gamma ray; and a processor configured
- to derive, in three dimensions, a distribution state of the nuclide in the imaging target and
- to determine information on a positron lifetime in association with a derived distribution position based on
- a detected energy and a detection position of each of the annihilation gamma rays as detected by the first gamma ray detector and
- a detection time point of the annihilation gamma rays as detected by the first gamma ray detector and a detection time point of the deexcitation gamma ray as detected by the second gamma ray detector, wherein the first gamma ray detector outputs a detection signal of a gamma ray that is incident on the first gamma ray detector, and in response to the second gamma ray detector detecting the deexcitation gamma ray, the processor acquires from the detection signal the detected energy and the detection position of each of the annihilation gamma rays and the detection time point of the annihilation gamma rays.

2. The PET system according to claim 1, wherein
the processor is configured
- to generate a three-dimensional distribution image of the nuclide in the imaging target and
- to derive the information on the positron lifetime individually at each of a plurality of positions in the three-dimensional distribution image based on
- the detected energy and the detection position of each of the annihilation gamma rays and
- the detection time point of the annihilation gamma rays and the detection time point of the deexcitation gamma ray.

3. The PET system according to claim 2, wherein
the processor is configured, for each event in which the three annihilation gamma rays have been measured coincidentally within a predetermined time of the detection time point of the deexcitation gamma ray,
- to estimate a positron annihilation position in the event and
- to derive, as a positron lifetime in the event, a time difference from the detection time point of the deexcitation gamma ray to a detection time point at which the three annihilation gamma rays have been measured coincidentally based on the detected energy and the detection position of each of the annihilation gamma rays, and the processor is configured further
- to generate the three-dimensional distribution image and
- to derive the information on the positron lifetime individually at a plurality of positions in the three-dimensional distribution image based on the positron annihilation position estimated and the positron lifetime derived for a plurality of events.

4. The PET system according to claim 1, wherein
the processor is configured to generate a positron lifetime image that shows, in three dimensions,
- distribution of the nuclide in the imaging target and
- information on the positron lifetime at each distribution position of the nuclide in the imaging target based on
- the detected energy and the detection position of each of the annihilation gamma rays and
- the detection time point of the annihilation gamma rays and the detection time point of the deexcitation gamma ray.

5. The PET system according to claim 4, wherein
the processor is configured, for each event in which the three annihilation gamma rays have been measured coincidentally within a predetermined time of the detection time point of the deexcitation gamma ray,
- to estimate a positron annihilation position in the event and
- to derive, as a positron lifetime in the event, a time difference from the detection time point of the deexcitation gamma ray to a detection time point at which the three annihilation gamma rays have been measured coincidentally based on the detected energy and the detection position of each of the annihilation gamma rays, and the processor is configured further
- to generate the positron lifetime image based on the positron annihilation position estimated and the positron lifetime derived for a plurality of events.

6. The PET system according to claim 1, wherein
when the second gamma ray detector detects the deexcitation gamma ray, the processor judges that an event has occurred, in response to occurrence of the event, the processor performs processing in which the processor checks whether or not the three annihilation gamma rays have been measured coincidentally within a predetermined time point of the deexcitation gamma ray, and through the processing, the processor acquires the detected energy and the detection position of each of the annihilation gamma rays and the detection time point of the annihilation gamma rays.

7. A method of measuring a lifetime of a positron in a PET system including a first gamma ray detector configured to receive, from an imaging target containing a nuclide that goes into an excited state of a daughter nucleus by undergoing beta decay and that then, subsequently to emission of a positron resulting from the beta decay, emits a deexcitation gamma ray when transiting into a ground state of the daughter nucleus, three annihilation gamma rays resulting from the positron annihilating with an electron, thereby to detect the three annihilation gamma rays, and a second gamma ray detector configured to detect the deexcitation gamma ray, the method comprising:

deriving, in three dimensions, a distribution state of the nuclide in the imaging target and determining information on a positron lifetime in association with a derived distribution position, based on a detected energy and a detection position of each of the annihilation gamma rays as detected by the first gamma ray detector and a detection time point of the annihilation gamma rays as detected by the first gamma ray detector and a detection time point of the deexcitation gamma ray as detected by the second gamma ray detector;

outputting, by the first gamma ray detector, a detection signal of a gamma ray that is incident on the first gamma ray detector; and acquiring from the detection signal the detected energy and the detection position of each of the annihilation gamma rays and the detection time point of the annihilation gamma rays in response to detection of the deexcitation gamma ray by the second gamma ray detector.

8. The method according to claim 7, further comprising:
judging that an event has occurred in response to detection of the deexcitation gamma ray by the second gamma ray detector; and
performing in response to occurrence of the event, processing comprising:
  checking whether or not the three annihilation gamma rays have been measured coincidentally within a predetermined time point of the deexcitation gamma ray; and
  acquiring the detected energy and the detection position of each of the annihilation gamma rays and the detection time point of the annihilation gamma rays.

* * * * *